(12) United States Patent
Takahashi

(10) Patent No.: US 10,912,682 B2
(45) Date of Patent: Feb. 9, 2021

(54) ABSORBENT ARTICLE

(71) Applicant: DAIO PAPER CORPORATION, Ehime (JP)

(72) Inventor: Aya Takahashi, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 359 days.

(21) Appl. No.: 15/757,774

(22) PCT Filed: Sep. 5, 2016

(86) PCT No.: PCT/JP2016/075998
§ 371 (c)(1),
(2) Date: Mar. 6, 2018

(87) PCT Pub. No.: WO2017/051695
PCT Pub. Date: Mar. 30, 2017

(65) Prior Publication Data
US 2018/0338872 A1    Nov. 29, 2018

(30) Foreign Application Priority Data

Sep. 25, 2015    (JP) ................................ 2015-188221

(51) Int. Cl.
*A61F 13/15* (2006.01)
*A61F 13/511* (2006.01)
(Continued)

(52) U.S. Cl.
CPC ...... *A61F 13/51108* (2013.01); *A61F 13/513* (2013.01); *A61F 13/51104* (2013.01);
(Continued)

(58) Field of Classification Search
CPC .............. A61F 13/51108; A61F 13/532; A61F 13/51104; A61F 13/513; A61F 13/15804;
(Continued)

(56) References Cited

U.S. PATENT DOCUMENTS 4,327,730 A * 5/1982 Sorensen .............. A61F 13/512
428/131
4,781,710 A    11/1988 Megison et al.
(Continued)

FOREIGN PATENT DOCUMENTS

CN    1976659    6/2007
EP    2656826    10/2013
(Continued)

OTHER PUBLICATIONS

International Search Report for PCT/JP2016/075998 dated Dec. 6, 2016.
(Continued)

*Primary Examiner* — Jacqueline F Stephens
(74) *Attorney, Agent, or Firm* — IPUSA, PLLC

(57) ABSTRACT

An absorbent article (200) includes an absorbent body (23) provided at a front and rear direction range including a crotch portion (C2), and a topsheet (22) that covers a top side of the absorbent body (23), wherein a slit (40) with a predetermined width is formed in the absorbent body (23) at least at the crotch portion (C2) to extend in a front and rear direction, and wherein the topsheet (22) includes a fall-in portion (30) that is fallen in the slit (40) of the absorbent body (23), and convex portions (31) are provided at least at a part of the fall-in portion (30).

5 Claims, 20 Drawing Sheets

(51) Int. Cl.
*A61F 13/532* (2006.01)
*A61F 13/513* (2006.01)

(52) U.S. Cl.
CPC ...... *A61F 13/532* (2013.01); *A61F 13/15804* (2013.01); *A61F 2013/51338* (2013.01)

(58) Field of Classification Search
CPC ........ A61F 2013/51338; A61F 13/5376; A61F 2013/53778; A61F 2013/51078
USPC .......................................... 604/378, 379, 380
See application file for complete search history.

(56) References Cited

U.S. PATENT DOCUMENTS

| | | | | |
|---|---|---|---|---|
| 4,846,821 | A * | 7/1989 | Lyons | A61F 13/51476 604/369 |
| 5,846,231 | A * | 12/1998 | Fujioka | A61F 13/515 604/380 |
| 6,563,013 | B1 * | 5/2003 | Murota | A61F 13/4704 604/379 |
| 2002/0065498 | A1 * | 5/2002 | Ohashi | A61F 13/536 604/379 |
| 2003/0143376 | A1 | 7/2003 | Toyoshima et al. | |
| 2006/0116653 | A1 | 6/2006 | Munakata et al. | |
| 2008/0262459 | A1 | 10/2008 | Kamoto et al. | |
| 2010/0063470 | A1 | 3/2010 | Suzuki et al. | |
| 2012/0220971 | A1 | 8/2012 | Harada et al. | |
| 2015/0250659 | A1 | 9/2015 | Tally et al. | |
| 2015/0290050 | A1 | 10/2015 | Wada | |
| 2017/0014280 | A1 | 1/2017 | Moritani | |
| 2017/0135869 | A1 | 5/2017 | Moriya et al. | |

FOREIGN PATENT DOCUMENTS

| | | |
|---|---|---|
| JP | 2620305 | 6/1997 |
| JP | H10-314217 | 12/1998 |
| JP | 2002-531172 | 9/2002 |
| JP | 2003-250836 | 9/2003 |
| JP | 2007-175248 | 7/2007 |
| JP | 2008-520401 | 6/2008 |
| JP | 2012-157380 | 8/2012 |
| JP | 2013-255557 | 12/2013 |
| JP | 2015-039579 | 3/2015 |
| JP | 2015-044046 | 3/2015 |
| JP | 2015-188453 | 11/2015 |
| JP | 2016-013209 | 1/2016 |
| JP | 2016-022282 | 2/2016 |
| WO | 2011/034180 | 3/2011 |
| WO | 2011/142272 | 11/2011 |
| WO | 2014/050310 | 4/2014 |

OTHER PUBLICATIONS

International Search Report for PCT/JP2017/004739 dated May 9, 2017.
Extended European search report for European Patent Application No. 17750331.5 dated Feb. 20, 2019.
Chinese Office Action for 201780010394.0 dated Jun. 23, 2020.
Office Action dated Oct. 2, 2020 issued to related U.S. Appl. No. 16/076,830.

* cited by examiner

FIG.5
(a)
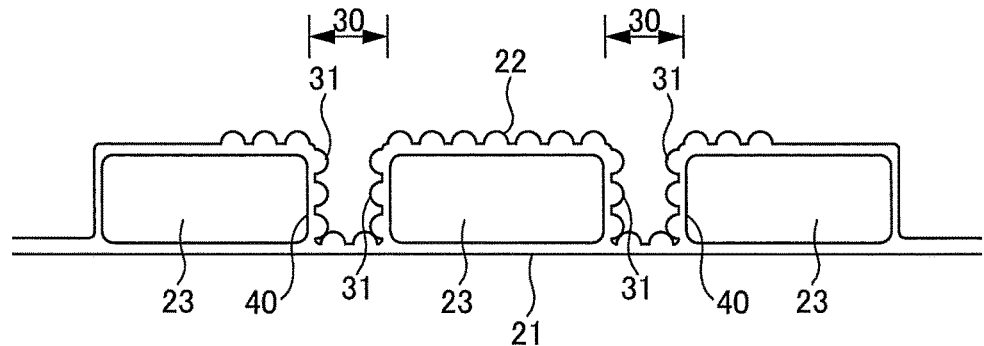
(b)
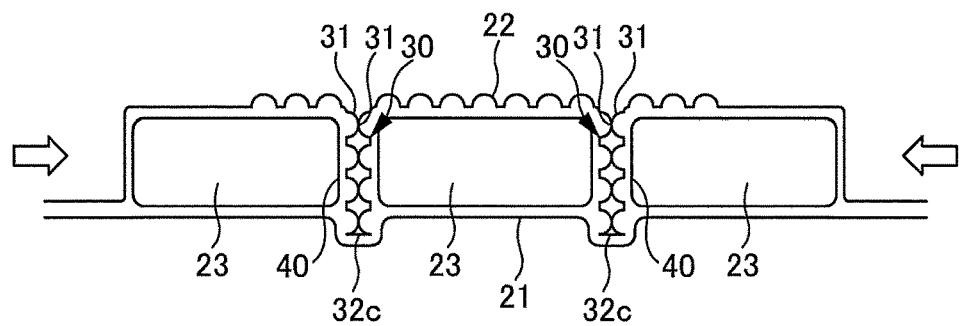
(c)
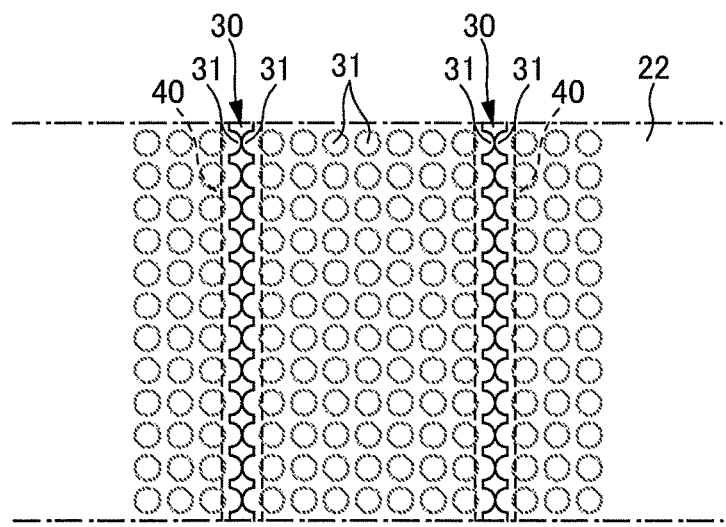

FIG.6
(a)
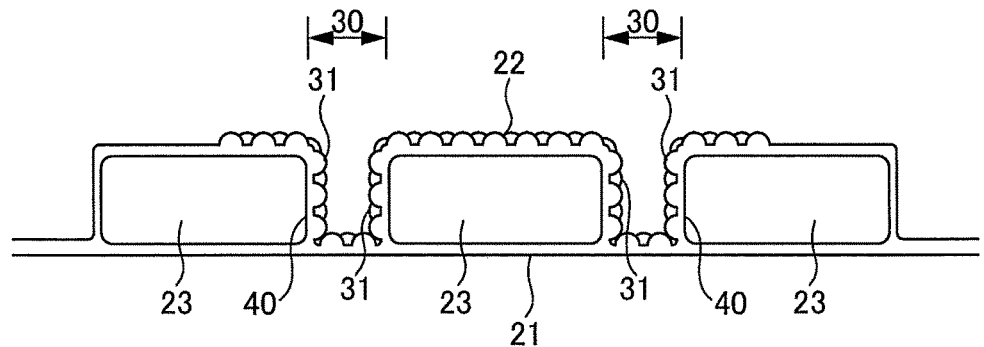
(b)
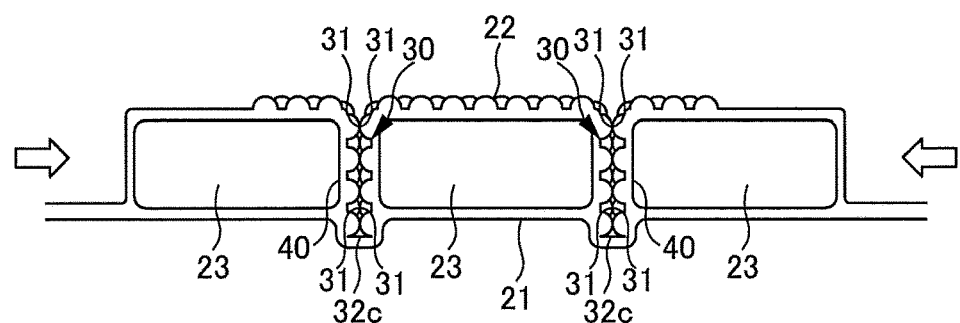
(c)
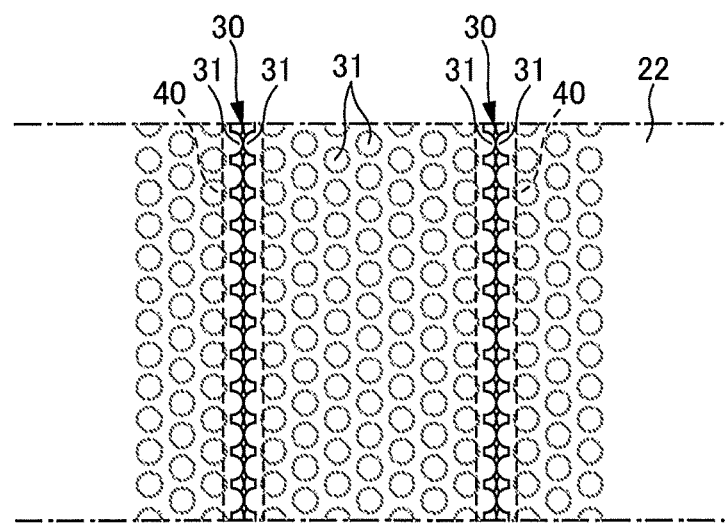

FIG.17
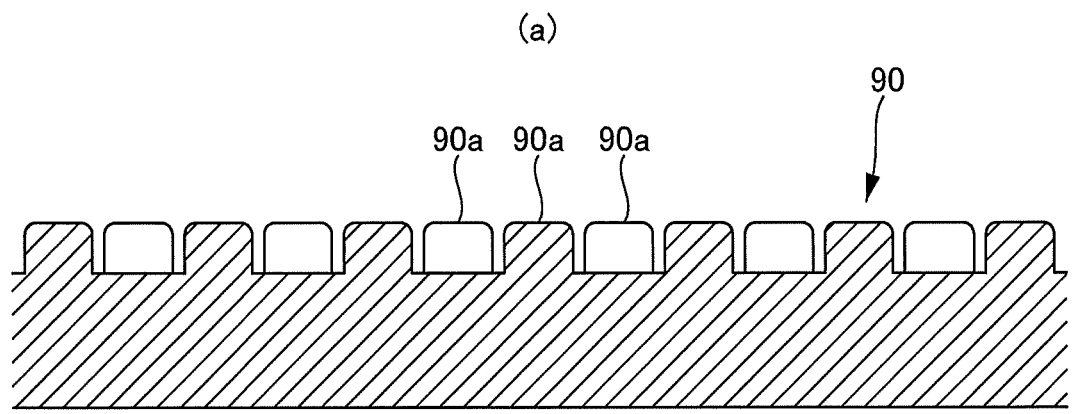
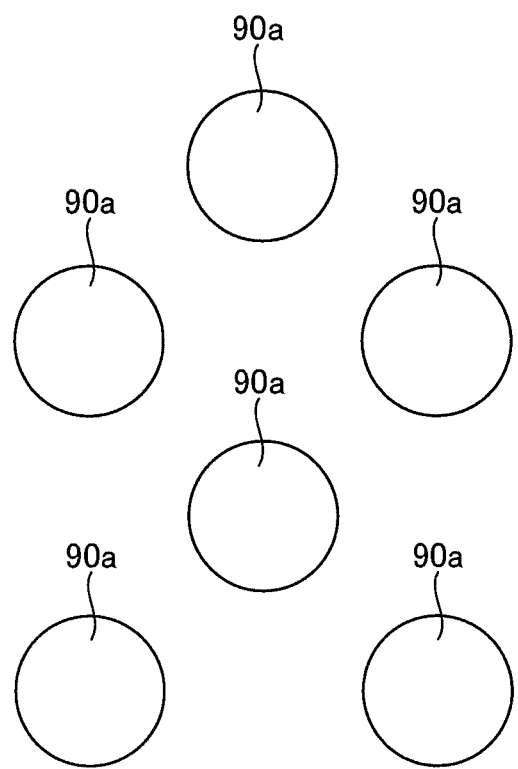

FIG.18
(a)
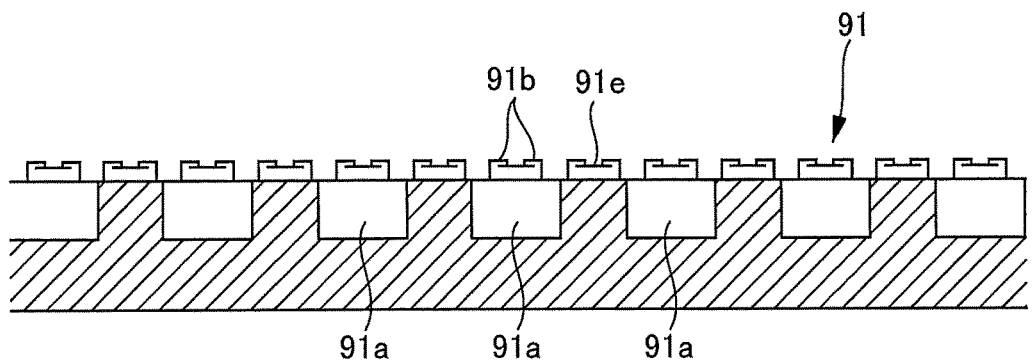
(b)
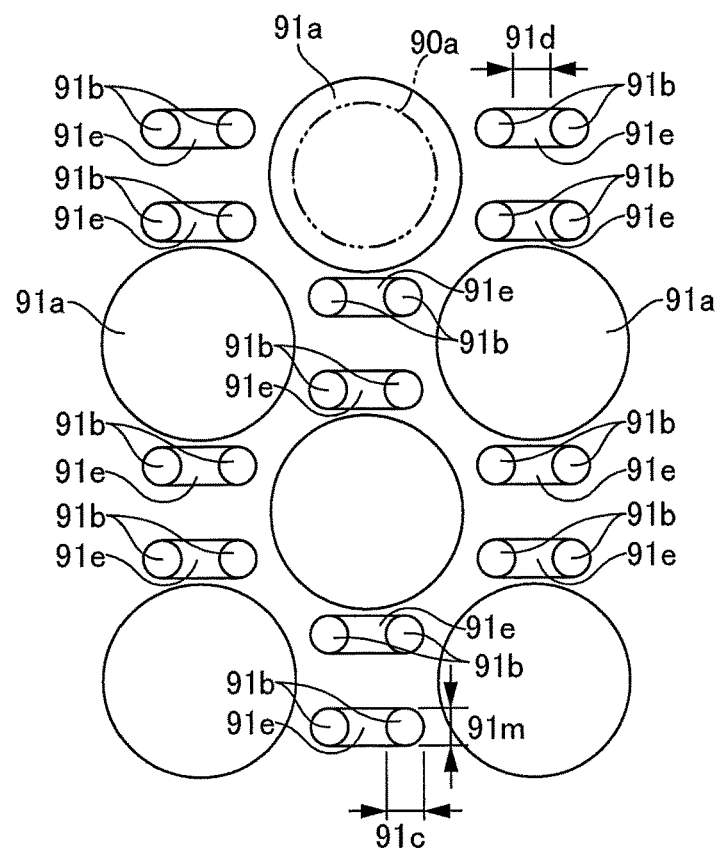

FIG.20
(a)
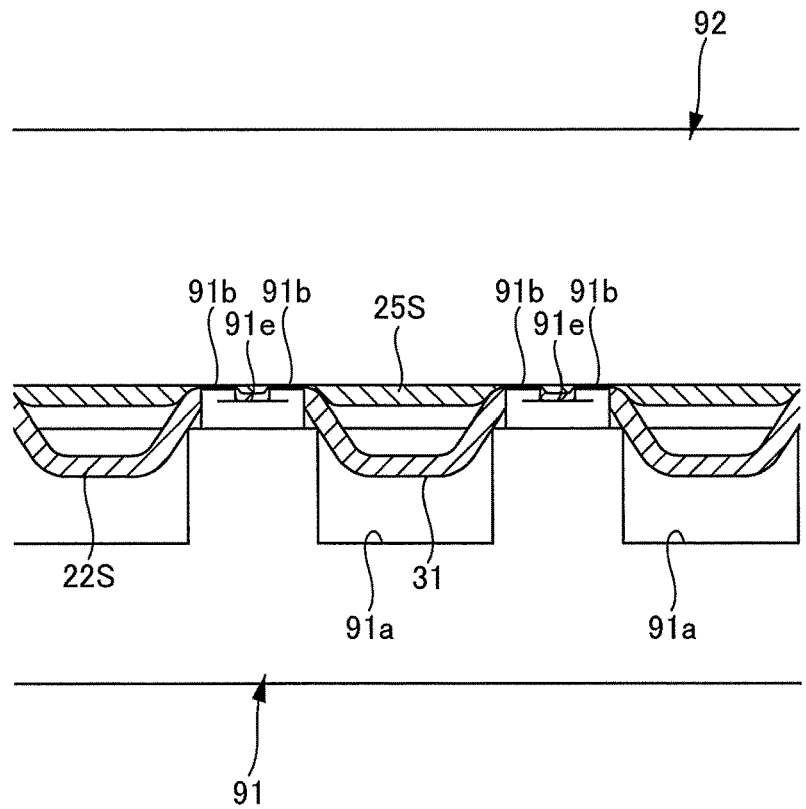
(b)
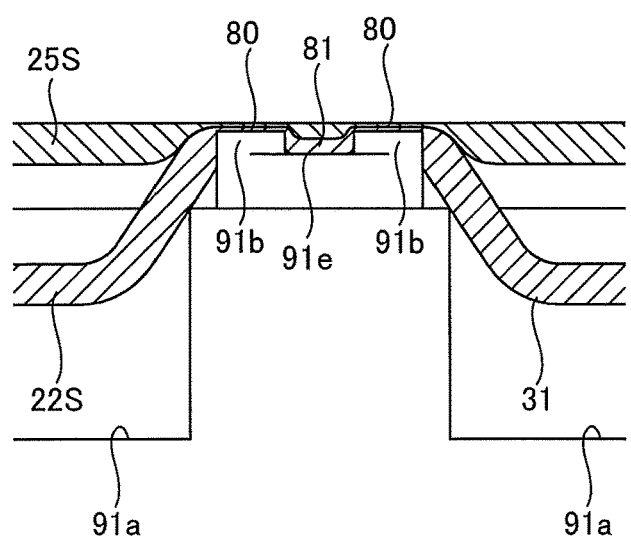

ABSORBENT ARTICLE

BACKGROUND OF THE INVENTION

1. Field of the Invention

The present invention relates to an absorbent article such as a disposal diaper or a sanitary napkin.

2. Description of the Related Art

When a wearer wears an absorbent article, a crotch portion of the absorbent article is sandwiched by both legs of the wearer, and is pressed to a certain extent in a width direction. A structure is known in which a slit or a concave groove extending in a front and rear direction with a predetermined width is provided at a region of an absorbent body in the front and rear direction including the crotch portion in order to improve diffusibility in the front and rear direction from an expelling site (see Patent Documents 1 and 2, for example).

PATENT DOCUMENTS

[Patent Document 1] Japanese Laid-open Patent Publication No. 2015-039579
[Patent Document 2] Japanese Laid-open Patent Publication No. 2012-157380

However, as described above, as the crotch portion is sandwiched by the both legs of the wearer and pressed to a certain extent in the width direction when the absorbent article is worn, the slit or the concave groove is retained while being collapsed in the width direction, and improvement of diffusibility may be prevented. This problem can be solved by making the width of the slit or the concave groove wider. However, in such a case, there is a problem that an absorption amount may be lowered and that a slit forming region of the absorbent body is deformed largely by the movement of the legs to cause twisting or tearing, and the shape of the slit is easily changed.

SUMMARY OF THE INVENTION

Thus, the purpose of the present invention is to suppress collapse of a slit or the like of an absorbent body.

According to the embodiment, there is provided an absorbent article including a crotch portion; a front side portion and a rear side portion that are extended toward a front side and a rear side of the crotch portion, respectively; an absorbent body provided at a front and rear direction range including the crotch portion; and a topsheet that covers a top side of the absorbent body, wherein a concave groove with a predetermined width that is concaved from a top surface to a back side or a slit with a predetermined width is formed in the absorbent body at least at the crotch portion to extend in a front and rear direction, and wherein the topsheet includes a fall-in portion that is fallen in the concave groove or the slit of the absorbent body, and convex portions are provided at least at a part of the fall-in portion.

As described above, according to the present invention, advantages such as collapse of a slit or the like of an absorbent body can be obtained.

BRIEF DESCRIPTION OF THE DRAWINGS

FIG. 5 is a view illustrating the pad type disposal diaper of the embodiment;
FIG. 6 is a view illustrating the pad type disposal diaper of the embodiment;
FIG. 17 is a view illustrating a pushing roller;
FIG. 18 is a view illustrating a concave roller;
FIG. 20 is an enlarged cross-sectional view illustrating a main part of a bonding step by the concave roller and the bonding roller.

DETAILED DESCRIPTION OF THE PREFERRED EMBODIMENTS

Hereinafter, embodiments of the invention are described in detail with reference to drawings. Among the terms of the invention, a "crotch portion" means a portion corresponding to a crotch of a body when wearing, and may be a region from a center or its vicinity to a predetermined site at a front side of an article in a front and rear direction as the illustrated embodiment, or a predetermined region at the center of the article in the front and rear direction, depending on products. When a constricted portion whose width is narrow is provided at a middle of the article in the front and rear direction or at a middle of an absorbent body in the front and rear direction, the "crotch portion" means a predetermined region in the front and rear direction having its center at a minimum width region of one of or both of the constricted portions in the front and rear direction. Further, a "front side portion (ventral portion)" means a portion at a front side of the crotch portion, and a "rear side portion (dorsal portion)" means a portion at a rear side of the crotch portion.

In the following embodiments, a pad type disposal diaper is described as an example of an absorbent article.

FIG. 1 to FIG. 4 illustrate an example of a pad type disposal diaper 200 of the invention. The pad type disposal diaper 200 includes a crotch portion C2, and a front side portion F2 and a rear side portion B2 that are extending in front and rear of the crotch portion C2, respectively. The size of each portion may be properly defined, and for example, the total length of the article (the length in the front and rear direction) L may be approximately 350 to 700 mm, and the total width W1 may be approximately 130 to 400 mm (here, this is wider than the width of an absorbing surface of the diaper). In such a case, the length of the crotch portion C2 in the front and rear direction is approximately 10 to 150 mm, the length of the front side portion F2 in the front and rear direction is approximately 50 to 350 mm, and the length of the rear side portion B2 in the front and rear direction is approximately 50 to 350 mm. Further, the width W3 of the crotch portion C2, for adults, may be greater than or equal to 150 cm, and particularly, may be approximately 200 to 260 cm.

Figure 3:
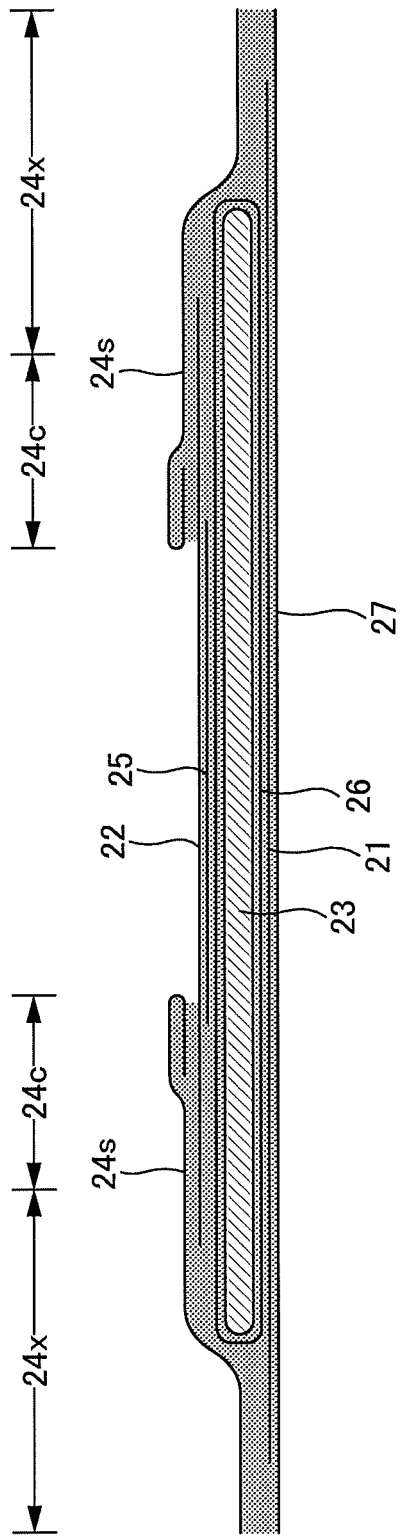
FIG. 3 is a cross-sectional view taken along Y-Y of FIG. 1.

As illustrated in FIG. 3, the pad type disposal diaper 200 has a basic structure in which an absorbent body 23 is disposed between an inner surface of a liquid impermeable sheet 21, on an outer surface of which an exterior sheet 27 is stacked, and a liquid permeable topsheet 22.

The liquid impermeable sheet 21 is provided at a back side of the absorbent body 23 so as to slightly protrude from a periphery of the absorbent body 23. As the liquid impermeable sheet 21, in addition to a polyethylene film or the like, a sheet having moisture permeability without losing a water shielding property may be used in order to prevent sweating. For such a water shielding and moisture permeability sheet, for example, a microporous sheet may be used that is obtained by forming a sheet by melting and kneading inorganic filler in olefin resin such as polyethylene or polypropylene and then extruding the sheet in one axial direction or two axial directions.

Further, the outer surface of the liquid impermeable sheet 21 is covered by the exterior sheet 27 made of a non-woven-fabric. The exterior sheet 27 is outwardly protruded from a periphery of the back sheet 21 with a predetermined protruding width. As the exterior sheet 27, various non-woven-fabrics may be used. As a material fiber for constituting the non-woven fabric, a synthetic fiber including an olefin series such as polyethylene or polypropylene, a polyester series, a polyamide series and the like, a regenerated fiber such as rayon or cupra (cuprammonium rayon), or a natural fiber such as cotton may be used.

A top side of the absorbent body 23 is covered by the liquid permeable topsheet 22. Although a part of the absorbent body 23 is protruded from side edges of the topsheet 22 in the illustrated embodiment, the width of the topsheet 22 may be extended such that side edges of the absorbent body 23 are not protruded. As the topsheet 22, a perforated or imperforate non-woven fabric or a porous plastic sheet may be used. As a material fiber for constituting the non-woven fabric, a synthetic fiber including an olefin series such as polyethylene or polypropylene, a polyester series, a polyamide series and the like, a regenerated fiber such as rayon or cupra (cuprammonium rayon), or a natural fiber such as cotton may be used.

It is preferable that an intermediate sheet 25 is disposed between the topsheet 22 and the absorbent body 23. The intermediate sheet 25 is provided to prevent flow back of urine absorbed in the absorbent body 23, and it is preferable that a material with a low water holding capacity and high permeability such as various non-woven-fabrics or mesh films are used, for example. When it is assumed that a front end of the topsheet 22 is 0%, and a rear end of the topsheet 22 is 100%, it is preferable that a front end of the intermediate sheet 25 is positioned within a range of 0 to 11%, and a rear end of the intermediate sheet 25 is positioned within a range of 92 to 100%. Further, it is preferable that the width W4 of the intermediate sheet 25 is approximately 50 to 100% of the minimum width W5 of a constricted portion 23n of the absorbent body 23, which will be described later.

At both end portions of the pad type disposal diaper 200 in the front and rear direction, the exterior sheet 27 and the liquid permeable topsheet 22 are extended further than both end sides of the absorbent body 23 at the front and rear ends to be adhered with each other, and end flap portions EF at which the absorbent body 23 does not exist are formed. The exterior sheet 27 is outwardly extended from side edges of the absorbent body 23 at both side portions of the pad type disposal diaper 200. Laterally outer portions 24x of gather sheets 24s that form standing gathers 24, respectively are adhered at an inner surface of the exterior sheet 27 from the extended portions to side portions of the topsheet 22 at the entirety in the front and rear direction to form side flaps SF at which the absorbent body 23 does not exist. These laminated portions are illustrated by dot patterns in FIG. 1, and may be formed by a hot-melt adhesive, a heat seal or ultrasonic sealing. When the exterior sheet 27 is not provided, the liquid impermeable sheet 21 may be extended to the side flaps SF instead of the exterior sheet 27 to form the outer surfaces of the side flaps SF.

As a material of the gather sheets 24s, a plastic sheet or a melt blown non-woven-fabric may be used, but preferably, a non-woven-fabric to which a water-repellent treatment is performed by silicon is used for improving feeling to skin.

Laterally center side portions 24c of the gather sheets 24s are extended over the topsheet 22, and elongated elastic members 24G are fixed at end portions at a center side in the width direction along the front and rear direction under an extended state by a hot-melt adhesive or the like. As the elongated elastic member 24G, a material that is normally used may be used such as a styrene series rubber, an olefin series rubber, a urethane series rubber, an ester series rubber, polyurethane, polyethylene, polystyrene, styrene-butadiene, silicon, polyester or the like that is formed into a threadlike form, a string-like form, a strip-like form or the like.

Figure 1:
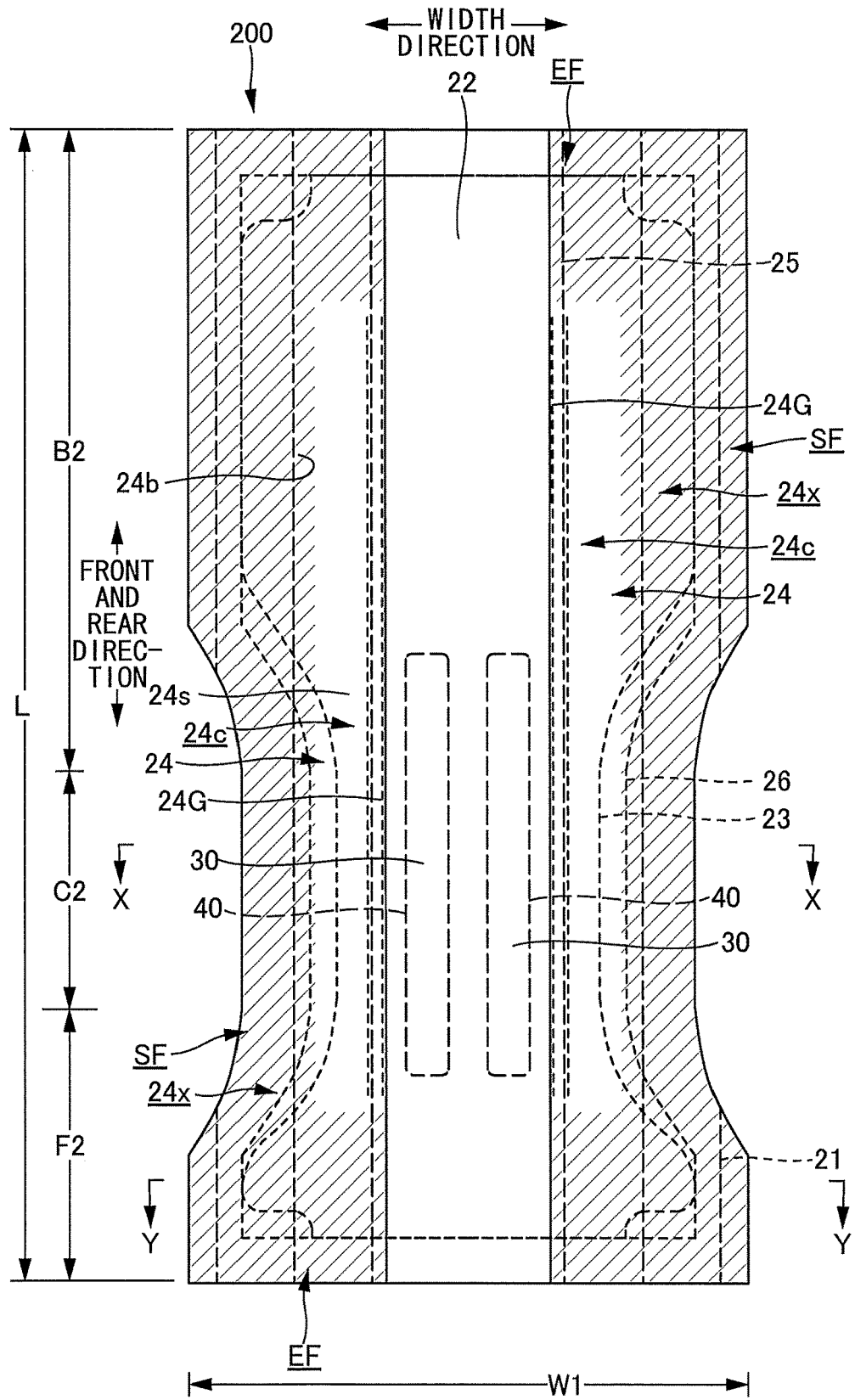
FIG. 1 is a plan view illustrating an inner surface side of a pad type disposal diaper at a spread state.

Further, the laterally outer portions 24x of the both of the gather sheets 24s are fixed by being adhered to an inner surface of the article (in the illustrated embodiment, the top surface of the topsheet 22 and the inner surface of the exterior sheet 27) over the entirety in the front and rear direction. Further, the laterally center portions 24c of the both of the gather sheets 24s are fixed by being adhered to the inner surface of the article (in the illustrated embodiment, the top surface of the topsheet 22) at both end portions in the front and rear direction, but are not fixed to the inner surface of the article (in the illustrated embodiment, the top surface of the topsheet 22) at a region between the both end portions in the front and rear direction. As illustrated in FIG. 1, this non-fixed portion functions as a leakage preventing wall that flexibly stands with respect to the inner surface of the article (in the illustrated embodiment, the top surface of the topsheet 22), and its standing base edge 24b is positioned on an interface of the laterally outer fixed portion 24x and the laterally center portion 24c of the gather sheet 24s.

As the absorbent body 23, a fiber stacking body of pulp fiber, aggregation of a filament such as cellulose acetate, or a non-woven-fabric may be used as a base, and a super absorbent polymer in a particle form or the like may be mixed, adhered or the like in accordance with necessity. The absorbent body 23 may be wrapped by a packaging sheet 26 such as a crepe paper, if necessary such as when the super absorbent polymer particles are mixed. Further, the shape of the absorbent body 23 may be formed into a proper shape such as a strip shape in which the width at a front side portion is relatively narrower than that at a rear side portion, or alternatively, a rectangular shape, a trapezoid shape or the like.

The fabric weight per unit area of the absorbent body 23 and the weight per unit area of the super absorbent polymer may be properly determined, and it is preferable that the fabric weight per unit area is approximately 100 to 600 g/m$^2$, and the weight per unit area of the absorbent polymer is approximately 0 to 400 g/m$^2$.

The absorbent body 23 is extended from the front side portion F2 toward the rear side portion B2, and in the illustrated embodiment, a predetermined portion including the crotch portion C2 at a middle in the front and rear direction is formed as the constricted portion 23*n* whose width is narrow. It is preferable that the minimum width W5 of the constricted portion 23*n* is approximately 50 to 65% of the width W2 of non-constricted portions positioned at front and rear of the constricted portion 23*n*, respectively. Further, when it is assumed that a front end of the article is 0% and a rear end of the article is 100%, it is preferable that a front end of the constricted portion 23*n* is positioned within a range of 10 to 25%. Further, it is preferable that a rear end of the constricted portion 23*n* is positioned within a range of 40 to 65%. Further, it is preferable that a site of the constricted portion 23*n* whose width becomes the minimum width W5 (minimum width region) is positioned within a range 25 to 30%.

Figure 2:
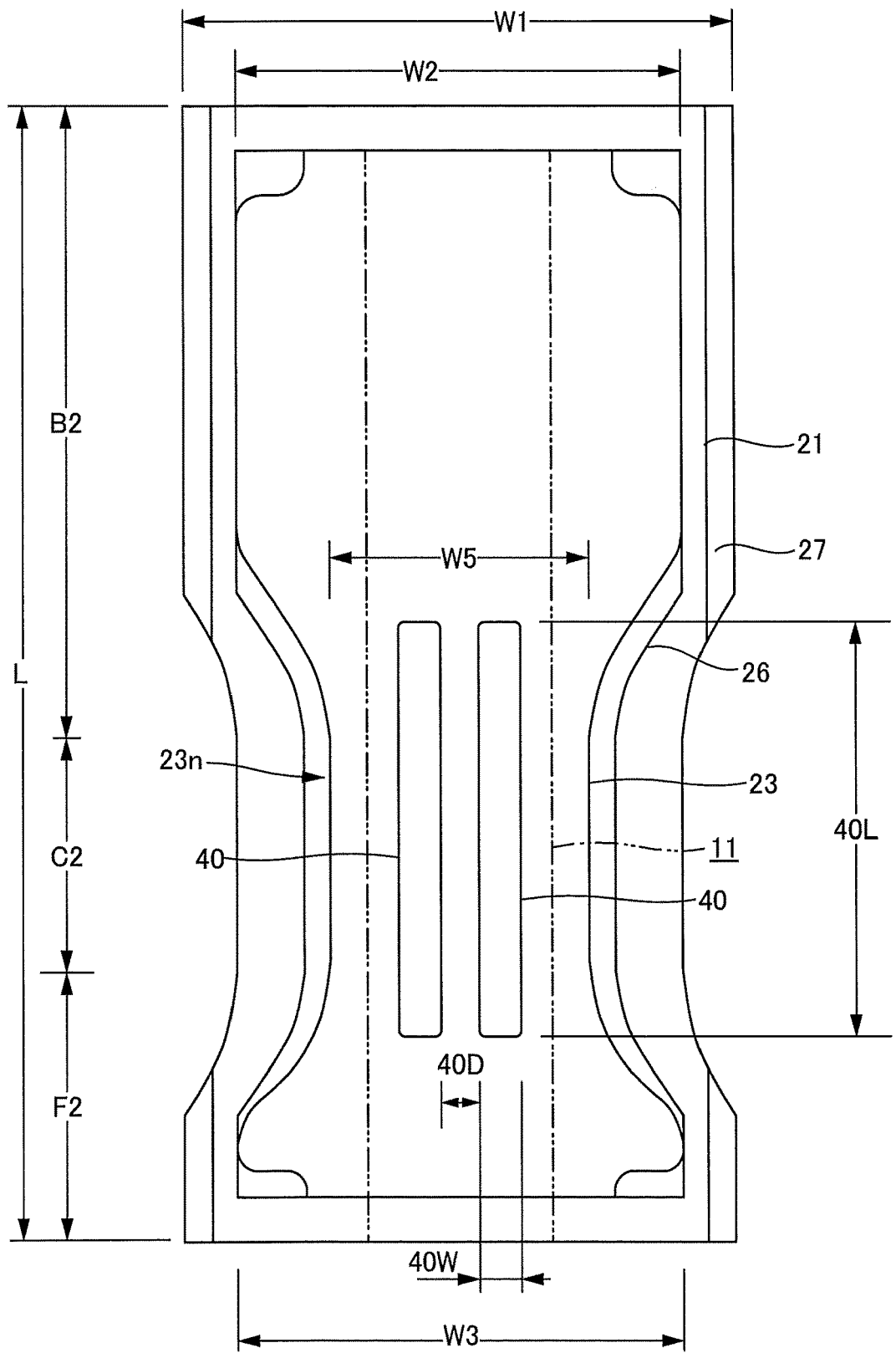
FIG. 2 is a plan view illustrating only a main portion.
Figure 4:
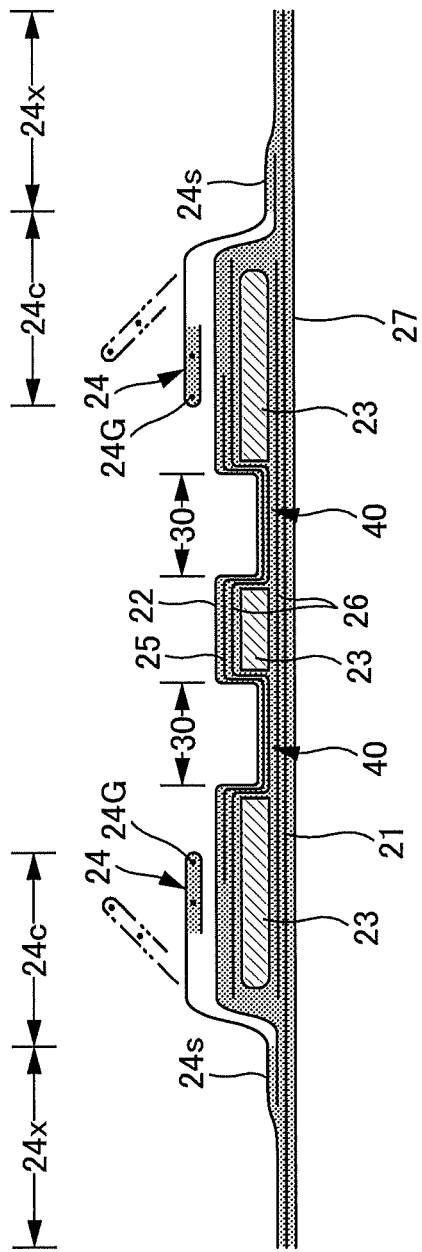
FIG. 4 is a cross-sectional view taken along X-X of FIG. 1.

In the pad type disposal diaper 200 of the embodiment, as illustrated in FIG. 1 and FIG. 2, slits 40, each with a predetermined width extending in the front and rear direction, are formed at a region corresponding to at least the crotch portion C2 in the front and rear direction in the absorbent body 23. Further, as illustrated in FIG. 4 to FIG. 6-(*c*), the topsheet 22 includes fall-in portions 30 that are fallen in the slits 40 of the absorbent body 23, respectively. As illustrated in FIG. 5-(*a*) to FIG. 6-(*c*), convex portions 31 are formed at least at a part of each of the fall-in portions 30 at the surface of the topsheet 22. Specifically, a plurality of the convex portions 31 are formed at least at a part of each of the fall-in portions 30 in a matrix form or in a staggered form. In the embodiment illustrated in FIG. 4, as top side portions of the intermediate sheet 25 and the packaging sheet 26 exist between the topsheet 22 and the absorbent body 23, these top side portions of the intermediate sheet 25 and the packaging sheet 26 are also fallen in each of the slits 40 with the topsheet 22. Here, the sheets other than the topsheet 22 may not be included.

As long as, the slits 40 are formed at the crotch portion C2, the length 40L in the front and rear direction is not particularly limited, and thus, the slits 40 may be provided over the entirety of the absorbent body 23 in the front and rear direction. However, it is preferable that the slits 40 are formed to extend from an end portion of the front side portion F2 at a crotch side to an end portion of the rear side portion B2 at a crotch side, as the illustrated embodiment.

Figure 7:
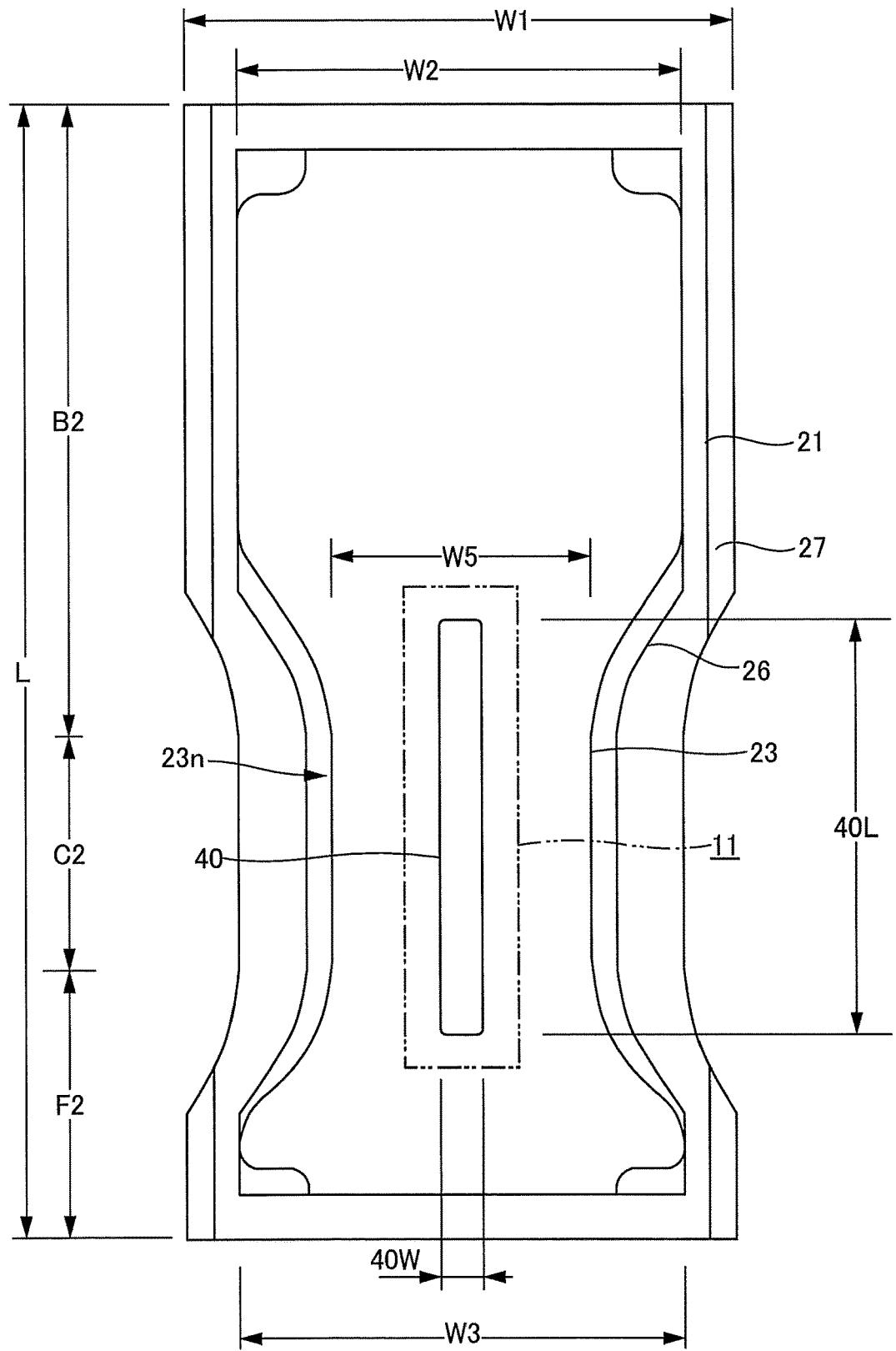
FIG. 7 is a plan view illustrating only a main portion of another example.
Figure 9:
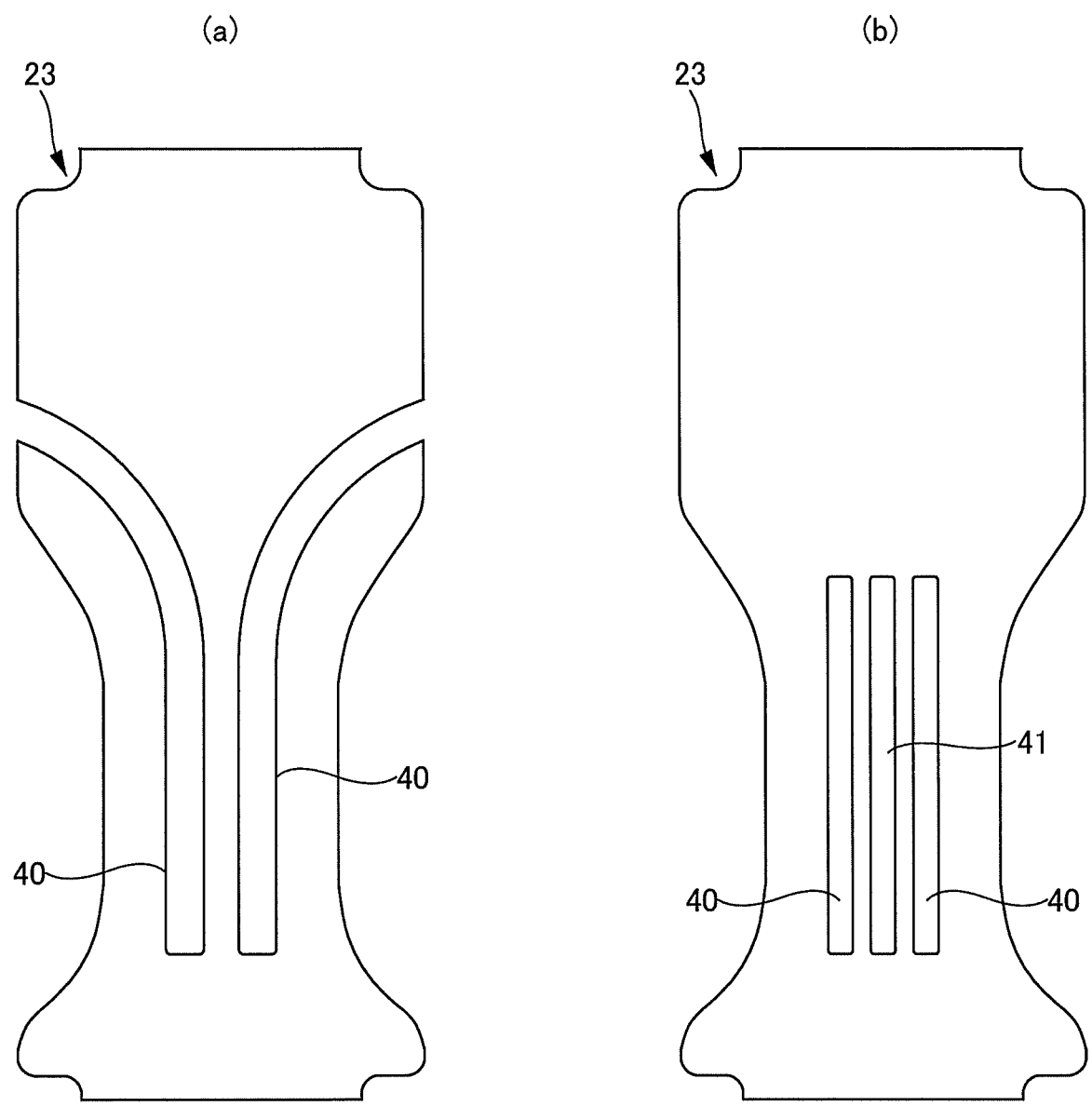
FIG. 9 is a plan view illustrating another example of the absorbent body of the embodiment.

FIG. 7, FIG. 9-(*a*) and FIG. 9-(*b*) are plan views illustrating another example of the absorbent body 23 of the embodiment. Further, as illustrated in FIG. 9-(*a*), a rear side portion of the slit 40 may be bent outwardly in the width direction (a front side portion may be similarly bent). More specifically, when it is assumed that a front end of the disposal diaper 200 is 0%, and a rear end of the disposal diaper 200 is 100%, it is preferable that a front end of the slit 40 is positioned within a range of 15 to 30%, and a rear end of the slit 40 is positioned within a range of 40 to 70%.

Although front and rear ends of each of the slits 40 are not extended to a periphery of the absorbent body 23 in the absorbent body 23 illustrated in FIG. 1 and FIG. 2, as the example illustrated in FIG. 9-(*a*), the rear end (alternatively front end or both ends) may be formed to reach the periphery. Here, for the embodiment in which both of the front and rear ends of each of the slits 40 reach the periphery of the absorbent body 23, portions that are positioned at sides of the slits 40 become bodies separated from a portion that is positioned between the slits 40.

Figure 8:
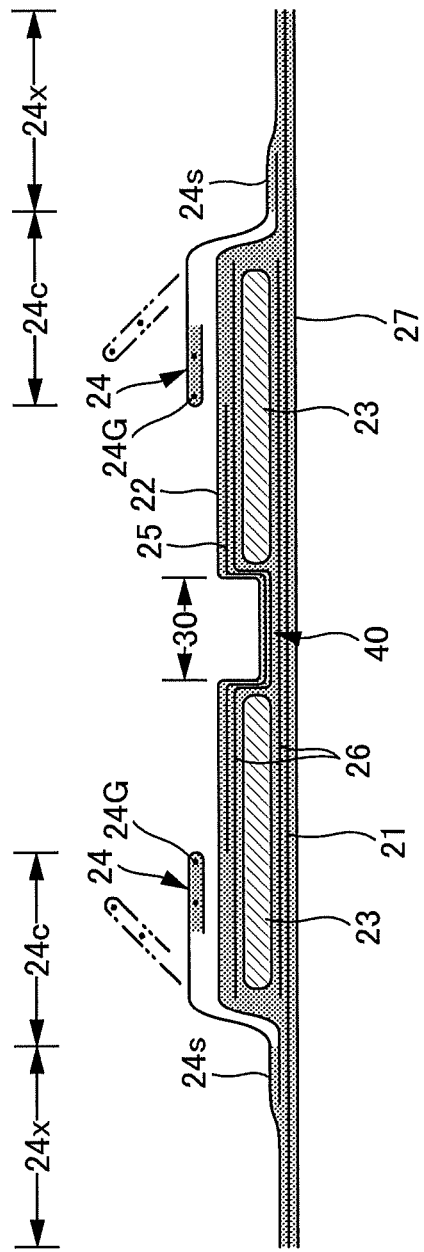
FIG. 8 is a cross-sectional view illustrating another example corresponding to an X-X cross-section of FIG. 1.

In addition to a case that the slit 40 is provided at each of the both sides in a lateral direction, a center slit 41 may be added at center in the width direction as illustrated in FIG. 9-(*b*). In such a case, it is preferable that the slits 40 are provided bilaterally symmetrical in the width direction, and normally, it is preferable that a distance 40D between the slits 40 is approximately 10 to 30% of the minimum width W5 of the constricted portion 23*n* of the absorbent body 23. The number of the slits 40 is not limited, and as illustrated in FIG. 7 and FIG. 8, only one slit may be provided at an intermediate portion in the width direction along the front and rear direction.

As long as facing side walls are apart from each other, the width 40W of the slit 40 is not particularly limited. Normally, it is preferable that the width 40W is approximately 10 to 20% of the minimum width W5 of the constricted portion 23*n* of the absorbent body 23, and specifically, for an adult product, may be approximately 5 to 32 mm.

FIG. 5-(*a*) is a cross-sectional view schematically illustrating a spread state of the pad type disposal diaper 200 of the embodiment. FIG. 5-(*b*) is a cross-sectional view schematically illustrating a worn state of the pad type disposal diaper 200 of the embodiment. FIG. 5-(*c*) is a plan view schematically illustrating a main part of the pad type disposal diaper 200 of the embodiment at the worn state. FIG. 6-(*a*) to FIG. 6-(*c*) illustrate another example. FIG. 6-(*a*) is a cross-sectional view schematically illustrating a spread state of the pad type disposal diaper 200 of the embodiment. FIG. 6-(*b*) is a cross-sectional view schematically illustrating a worn state of the pad type disposal diaper 200 of the embodiment. FIG. 6-(*c*) is a plan view schematically illustrating a main part of the pad type disposal diaper 200 of the embodiment at the worn state. In FIG. 5-(*a*) to FIG. 5-(*c*), the convex portions 31 are arranged in a matrix form, and in FIG. 6-(*a*) to FIG. 6-(*c*), the convex portions 31 are arranged in a staggered form (an arrangement in which the convex portions are alternately provided in adjacent lines).

In the pad type disposal diaper 200 configured as described above, as can be understood from the comparison between the spread state illustrated in FIG. 5-(*a*) and the worn state illustrated in FIG. 5-(*b*) and FIG. 5-(*c*), or the comparison between the spread state illustrated in FIG. 6-(*a*) and the worn state illustrated in FIG. 6-(*b*) and FIG. 6-(*c*), the crotch portion C2 is sandwiched between both legs of a wearer at the worn state. Thus, when the crotch portion C2 is compressed to a certain extent in the width direction and both side surfaces of the slit 40 approach with each other, if the convex portion 31 is positioned at a bottom portion of the fall-in portion 30, a space can be retained between the facing side surfaces as the convex portion 31 is sandwiched by the facing side surfaces. Further, if the convex portion 31 is positioned at one of the facing side surfaces, a space can be retained between the periphery of the convex portion 31 and the facing side surface as the convex portion 31 contacts the other of the facing side surfaces. Thus, collapse of the slit 40 can be suppressed, and an effect of improving diffusibility by the slit 40 can be retained.

The convex portions 31 of the topsheet 22 may be only provided in the fall-in portion 30, in other words, may be only provided in the slit 40, and may be provided at one of the slits 40 of the in the width direction. Further, the number of the convex portions 31 is not limited, and may be small. However, it is difficult to manufacture such that the position of the convex portion 31 precisely matches the position of the slit 40 of the absorbent body 23. Thus, it is preferable that the number of the convex portions 31 are aligned with a space therebetween in the width direction and in the front and rear direction as illustrated in FIG. 5-(a) to FIG. 5-(c) and FIG. 6-(a) to FIG. 6-(c), at a range 11 that includes the fall-in portion(s) 30 of the topsheet 22 and that is wider (larger) than the fall-in portion 30(s) as illustrated in FIG. 2 and FIG. 7. For example, as illustrated in FIG. 2, an arrangement region 11 of the convex portions 31 may be provided at the entirety of the topsheet 22 in the front and rear direction, or alternatively, as illustrated in FIG. 7, the arrangement region 11 may be provided to slightly extend over the front and rear ends of the slit 40. For the width direction, the convex portions 31 may be aligned at the entirety of the width of the topsheet 22, or alternatively, as the illustrated example, the convex portions 31 may be provided to slightly extend over both ends of the slit(s) 40 in the width direction. When a plurality of the slits 40 are provided with a space therebetween in the width direction, although not illustrated in the drawings, a plurality of the arrangement regions of the convex portions 31 may be provided with a space therebetween in the width direction as well.

When the number of the convex portions 31 are aligned with a space therebetween in the width direction and in the front and rear direction over the range 11 that includes the fall-in portions 30 of the topsheet 22 and that is wider (larger) than the fall-in portions 30, a single line of the convex portions 31 aligned in the front and rear direction may be provided in each of the fall-in portions 30. However, as illustrated in FIG. 5-(a) to FIG. 5-(c) and FIG. 6-(a) to FIG. 6-(c), it is preferable that a plurality of such lines are formed because even when the position of the topsheet 22 in the width direction with respect to the absorbent body 23 is slightly shifted when being manufactured or when being used, either of the lines of the convex portions 31 can retain the space of the respective slit 40 in its extending direction.

Figure 11:
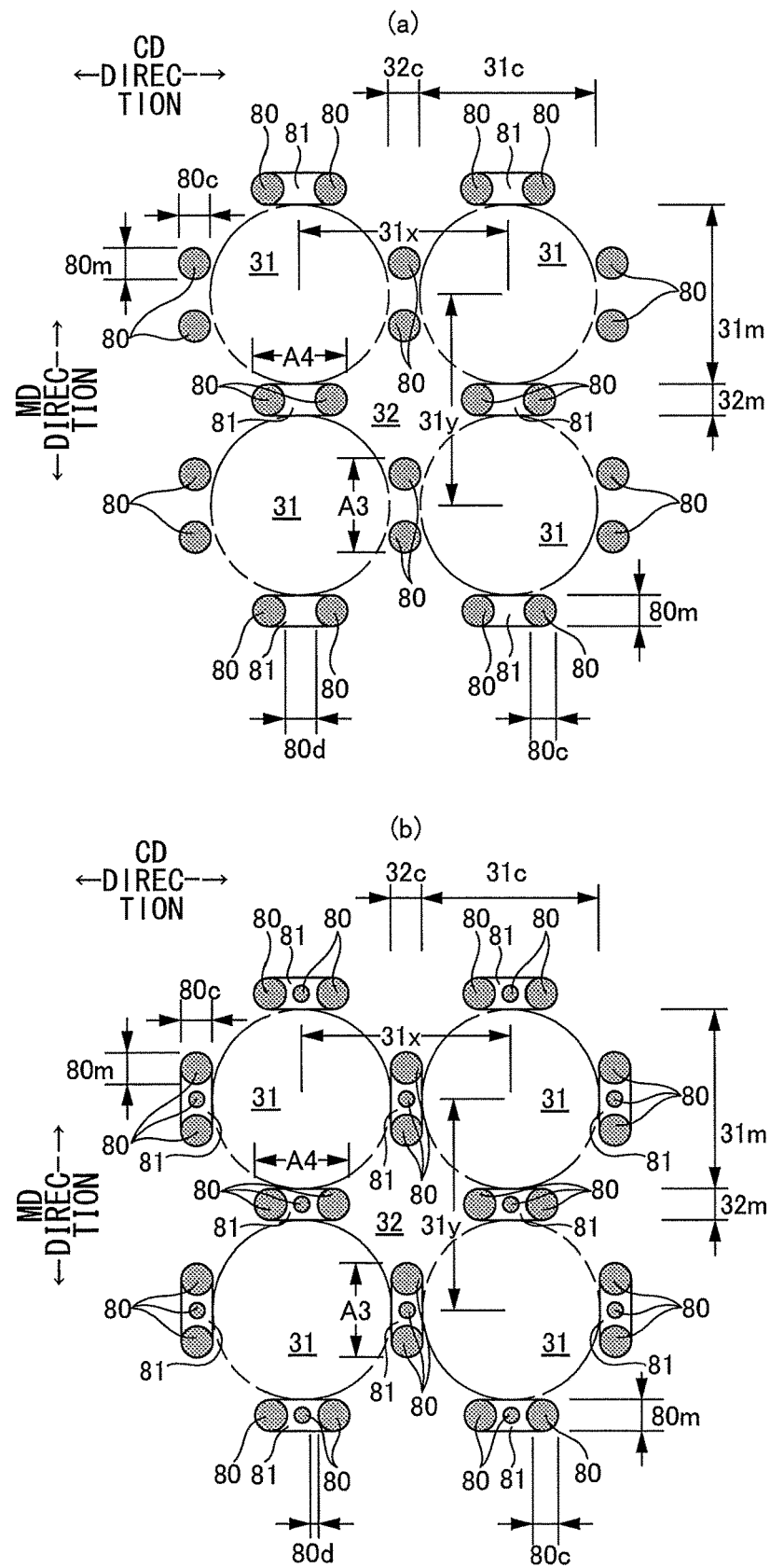
FIG. 11 is an enlarged plan view illustrating an example of a bonding pattern of a topsheet bonding portion.

Further, as illustrated in FIG. 11-(a) to FIG. 12-(b), which will be described later, when a number of the convex portions 31 are aligned with a space therebetween in the width direction and in the front and rear direction, it is preferable that the size 31m of the convex portion 31 in the front and rear direction is larger than a distance 32m between the convex portions 31 that are adjacent in the front and rear direction. Similarly, it is preferable that the size 31c of the convex portion 31 in the width direction is larger than a distance 32c between the convex portions 31 that are aligned in the width direction. If the size 31m or 31c of the convex portion 31 is small and the distance 32m or 32c between the convex portions 31 is too large, or the convex portion 31 can fit the space 32 between the adjacent convex portions, the above described function of retaining the space may be obtained only locally. On the other hand, if the sizes 31m and 31c of the convex portion 31 are larger than the distances 32m and 32c between the convex portions 31, area occupied by the convex portions 31 becomes larger than that by the spaces between the convex portions 31. Thus, in any arrangements, and also even if the fall-in portion 30 is deformed in any shapes, the convex portion 31 of one of the facing side surfaces does not enter the space between the convex portions 31 of the other of the facing side surfaces, and the facing convex portions 31 can contact with each other to ensure preferable spaces.

As illustrated in FIG. 5-(a) to FIG. 5-(c), when the convex portions 31 are aligned in a matrix form, it is preferable that the distance 32c between the convex portions 31 that are adjacent in the width direction is 0.1 to 0.5 times of the size 31c of the convex portion 31 in the width direction. This means, as illustrated in FIG. 11-(a) and FIG. 11-(b), when the convex portions 31 are aligned in a matrix form, a portion between the convex portions 31 (a portion with low rigidity) linearly continuously extend longest in the front and rear direction at the space 32c between the convex portions 31 that are adjacent in the width direction. Thus, when the width of the slit 40 is narrowed, the topsheet 22 is bent at this position 32c. At this time, if the convex portions 31 are aligned with the above described size 31c and the distance 32c, the convex portion 31 of one of the facing side surfaces does not enter the space between the convex portions 31 of the other of the facing side surfaces, and the facing convex portions 31 contact with each other to ensure preferable spaces.

Further, as illustrated in FIG. 6-(a) to FIG. 6-(c), when the convex portions 31 are aligned in a staggered form, it is preferable that the distance between the convex portions 31 that are adjacent in the width direction is 0.5 to 0.9 times of the size of the convex portion 31 in the width direction. As illustrated in FIG. 12-(a) and FIG. 12-(b) as well, when the convex portions 31 are aligned in a staggered form, a portion between the convex portions 31 (a portion with low rigidity) linearly continuously extend longest in the front and rear direction at a center in the width direction of the convex portions 31 that are aligned in a zig-zag manner in the front and rear direction. Thus, when the width of the slit 40 is narrowed, the topsheet 22 is bent at this position Q. Here, if the convex portions 31 are aligned with the above described size and the distance, the convex portion 31 of one of the facing side surfaces does not enter between the convex portions 31 of the other of the facing side surfaces, and the facing convex portions 31 contact with each other to ensure preferable spaces.

Specific size, shape, arrangement and structure of the convex portion 31 of the topsheet 22 are not specifically limited, and may be properly determined. The following is an example.

Figure 10:
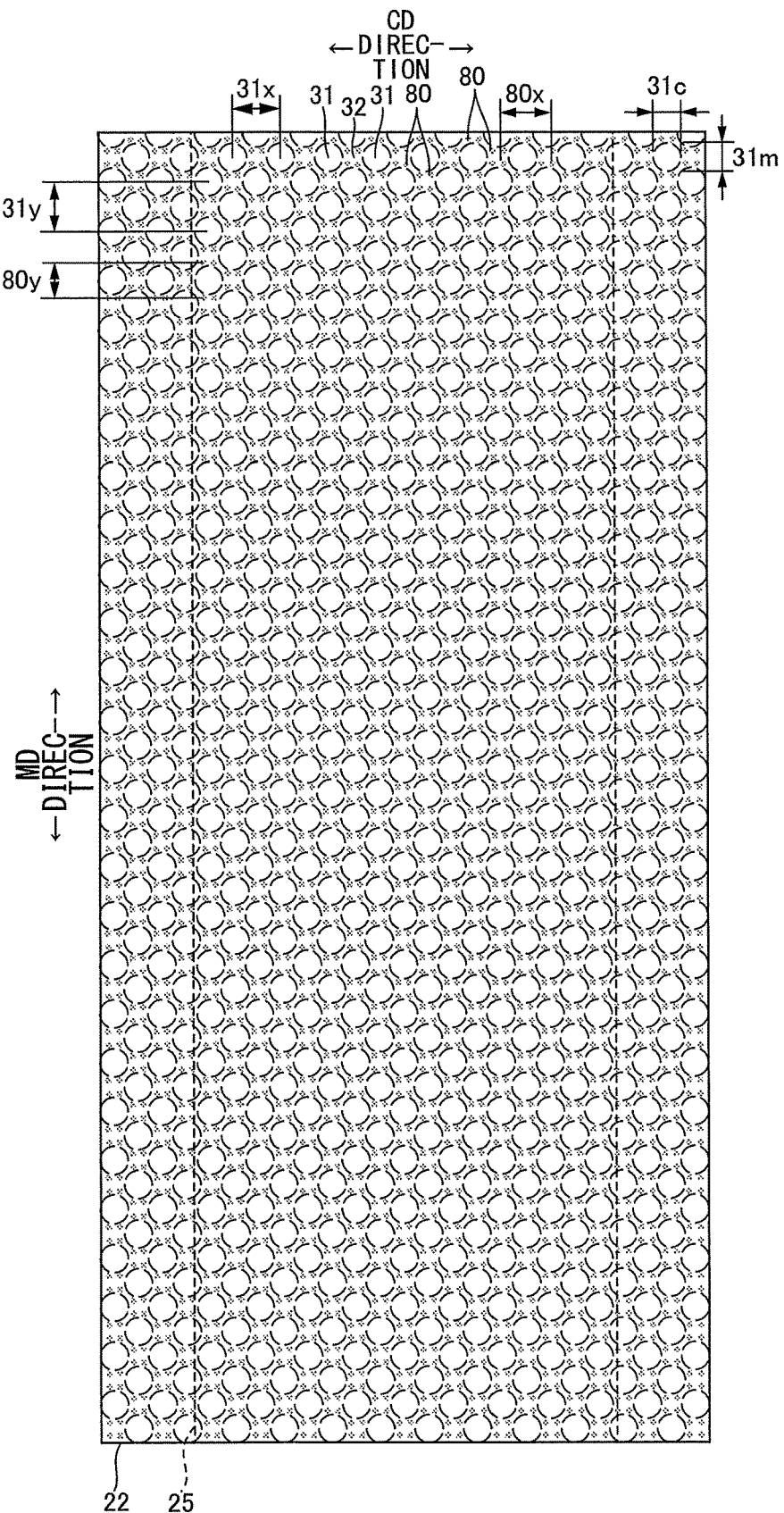
FIG. 10 is a plan view of a topsheet and an intermediate sheet.
Figure 12:
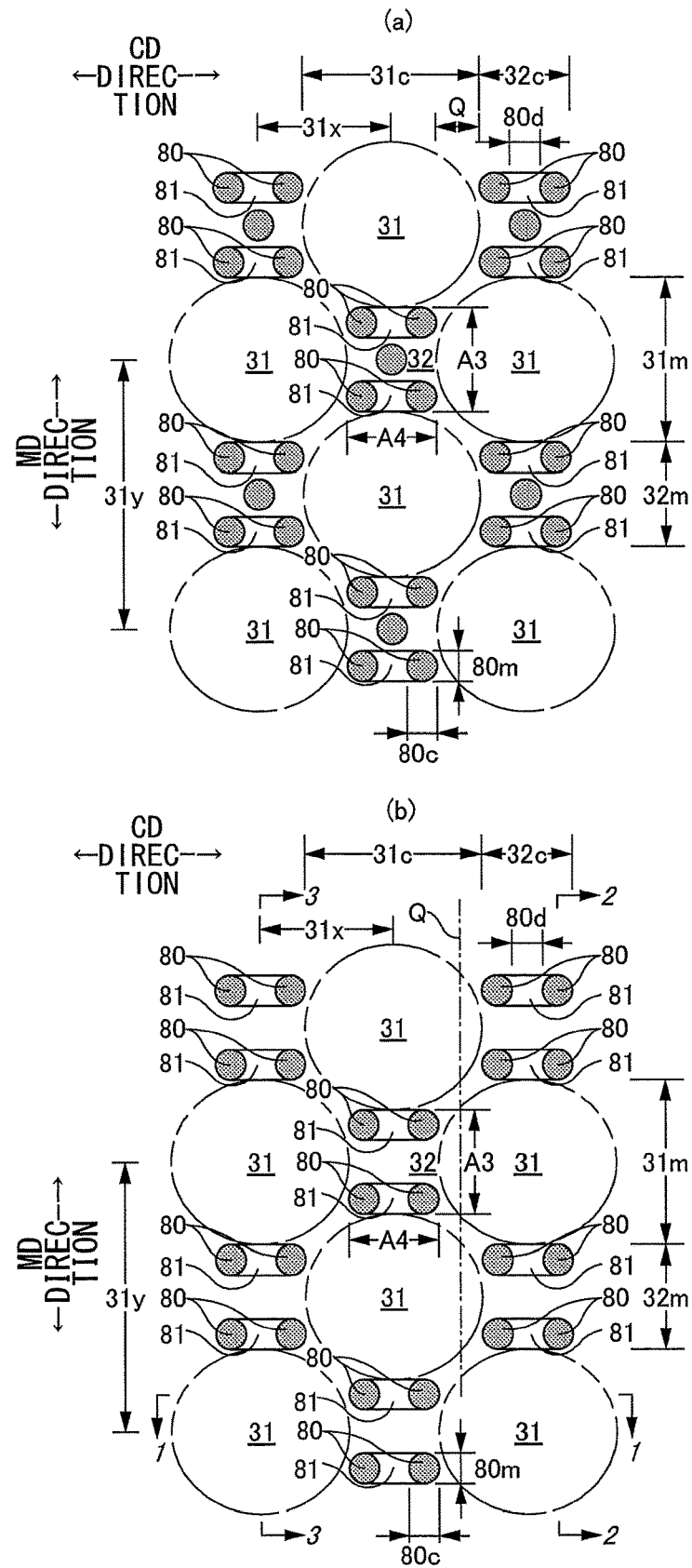
FIG. 12 is an enlarged plan view illustrating an example of the bonding pattern of the topsheet bonding portion.

Specifically, as illustrated in FIG. 10 to FIG. 13-(c), the number of convex portions 31 may be aligned with a space therebetween in the width direction and in the front and rear direction, respectively, by extruding the topsheet 22 from the back side to the top side by embossing. Here, the numeral "32" indicates a portion between the adjacent convex portions 31. Arrangement of the convex portions 31 may be properly changed such as being aligned in a matrix form as illustrated in FIG. 11-(a) and FIG. 11-(b), or aligned in a staggered form (an arrangement in which the convex portions are alternately provided in adjacent lines) as illustrated in FIG. 10, FIG. 12-(a) and FIG. 12-(b). Further, although an embodiment in which the convex portions 31 are provided at almost the entirety of the topsheet 22 is assumed in the illustrated embodiment, as described above, the convex portions 31 may be partially provided as long as the convex portions 31 are provided at least at the regions corresponding to the both side portions of the first portion 11, and the regions that are adjacent to them at outsides in the width direction. For example, the convex portions 31 may be provided at almost the entirety of the region where the topsheet 22 and the intermediate sheet 25 overlap.

The size and the like of the convex portion 31 may be properly determined, and as illustrated in FIG. 10 to FIG. 12-(b), the size 31m of the convex portion 31 in a MD (machine direction) direction is less than or equal to a distance 80y between centers of a topsheet bonding portion 80 (described later) positioned at one side of the convex portion 31 and a topsheet bonding portion 80 positioned at the other side of the convex portion 31 in the MD direction, and it is preferable that its lower limit is approximately 0.9 times, and normally, approximately 2.7 to 9 mm. Similarly, it is preferable that the size 31c of the convex portion 31 in a CD (cross direction) direction is less than or equal to a distance 80x between centers of a topsheet bonding portion 80 positioned at one side of the convex portion 31 in the CD direction and a topsheet bonding portion 80 positioned at the other side of the convex portion 31 in the CD direction, and it is preferable that its lower limit is approximately 0.9 times, and normally, approximately 2.7 to 9 mm. Further, it is preferable that the height 31z of the convex portion 31 is, normally, approximately 0.8 to 2 mm.

Here, the "MD direction" and the "CD direction" of a product mean a "MD direction" and a "CD direction" of a processing plant of the convex portion 31, and one of them becomes the front and rear direction and the other of them becomes the width direction. Then, the MD direction of the product is a direction of a fiber orientation of the non-woven-fabric of the topsheet 22. The fiber orientation is a direction in which the fibers of the non-woven-fabric extend, and may be determined by, for example, a measurement method according to TAPPI STD T481, fiber orientation testing by zero-span tensile strength, or a simple measurement method by which the fiber orientation is decided from the tensile strength ratio in the front and rear direction and in the width direction. In the illustrated embodiment, similar to the almost all of absorbent article products, the front and rear direction is the MD direction and the width direction is the CD direction.

Although the distance between the convex portions 31 may be properly determined, for the case of the matrix form as illustrated in FIG. 11-(a) and FIG. 11-(b), it is preferable that a distance 31x in the CD direction between centers of the convex portions 31 of the MD direction lines that are adjacent in the CD direction is approximately 3 to 10 mm, and a distance 31y in the MD direction between centers of the convex portions 31 of the CD direction lines that are adjacent in the MD direction is approximately 3 to 10 mm. Further, for the case of the staggered form as illustrated in FIG. 10, FIG. 12-(a) and FIG. 12-(b), it is preferable that a distance 31x in the CD direction between centers of the convex portions 31 of the MD direction lines that are adjacent in the CD direction is approximately 3 to 10 mm, and a distance 31y in the MD direction between centers of the convex portions 31 of the CD direction lines that are adjacent in the MD direction is approximately 3 to 10 mm.

Although it is preferable that the convex portion 31 is formed into a circular dome shape, the convex portion 31 may be formed into an elliptical dome shape or a regular polygonal dome shape. The convex portions 31 may be formed by embossing the topsheet 22.

As illustrated in FIG. 10 to FIG. 12-(b) as well, when portions of the topsheet 22 between the adjacent convex portions 31 in the width direction and in the front and rear direction are pressed and welded (adhered) with the intermediate sheet 25, a number of topsheet bonding portions 80 are formed as intermittent bonding patterns in the width direction and in the front and rear direction. The topsheet bonding portion 80 is also a portion at which a bottom portion of the concave portion is formed. In the bonding pattern of the topsheet 22 and the intermediate sheet 25 of the embodiment, in a region between the convex portions 31 that are adjacent in the MD direction, a line in which a plurality of topsheet bonding portions 80 are aligned in the CD direction with a space therebetween is formed to across a center position of the region in the CD direction. Further, at a space between the topsheet bonding portions 80 in the CD direction, the topsheet 22 and the intermediate sheet 25 are not welded and the topsheet 22 is formed as a pressed portion 81 that is more compressed than both sides in the MD direction.

Figure 13:
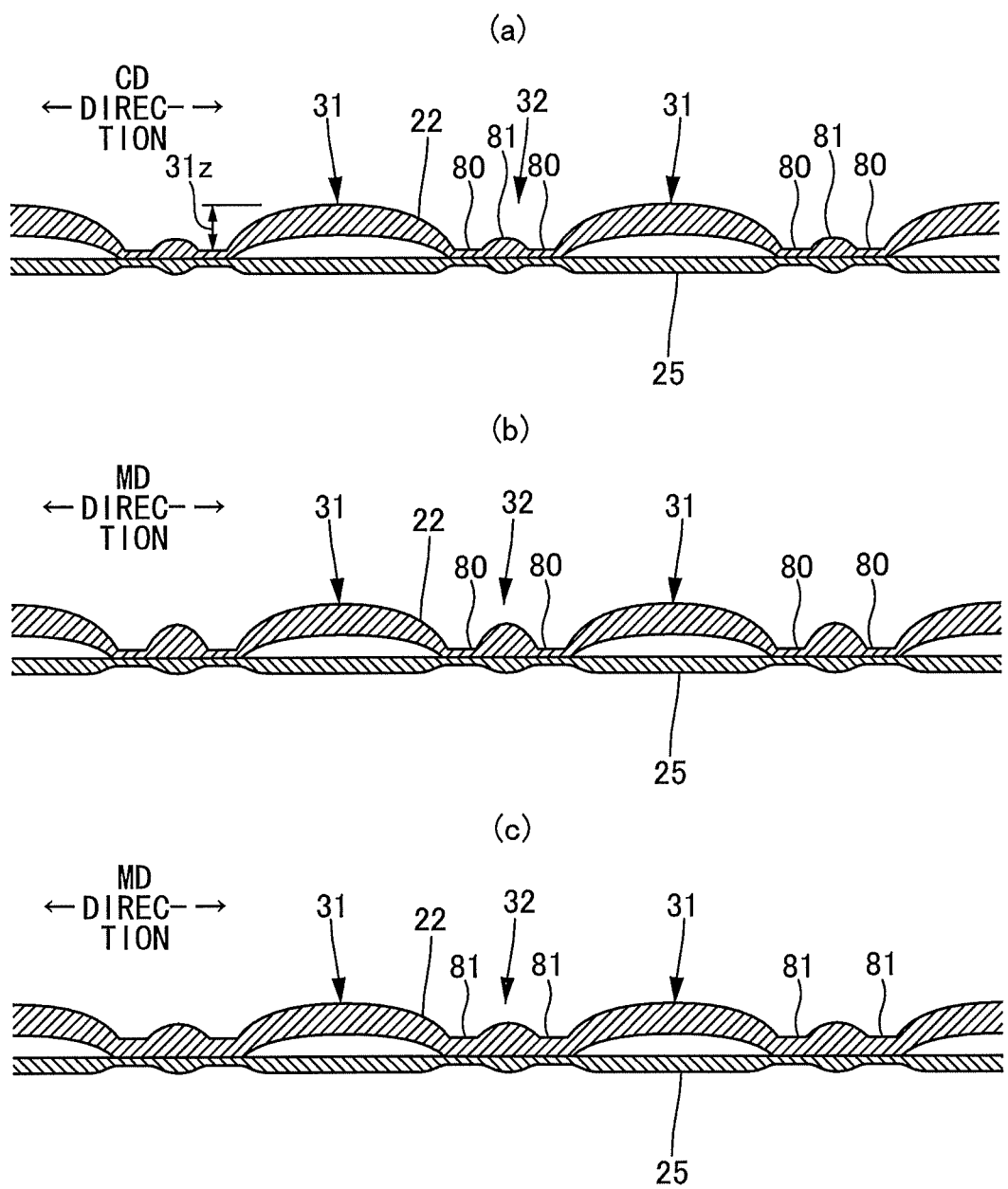
FIG. 13 is a cross-sectional view of FIG. 12-(b)

FIG. 13-(a), FIG. 13-(b) and FIG. 13-(c) are cross-sections of FIG. 12-(b) taken along 1-1, 2-2 and 3-3, respectively. As long as the topsheet 22 is pressed at the pressed portion 81, the intermediate sheet 25 may be integrally pressed with the topsheet 22, or may not be pressed. Further, although the topsheet 22 and the intermediate sheet 25 may not be welded and also may be pressed at portions other than the topsheet bonding portions 80 and the pressed portions 81 similarly as the space portions (81) in the CD direction, it is preferable that the topsheet 22 and the intermediate sheet 25 are not welded and also the topsheet 22 is pressed less than at the space portions in the CD direction (including a non-pressed state, where the topsheet 22 is not pressed at all).

In other words, when it is assumed that, in the topsheet 22, the thickness of the topsheet bonding portion 80 is T1, the thickness of the pressed portion 81 is T2 and the thickness of the portion other than the topsheet bonding portion 80 and the pressed portion 81 is T3, the relationship may be T1<T2=T3, but preferably, T1<T2<T3. Further, although a space is formed between a portion of the topsheet 22 that has the convex portion 31 and the intermediate sheet 25 in the embodiment illustrated in FIG. 13-(a) to FIG. 13-(c), such a space may not be formed, and in such a case, the entirety of the back surface of the topsheet 22 and the intermediate sheet 25 may be adhered.

Figure 15:
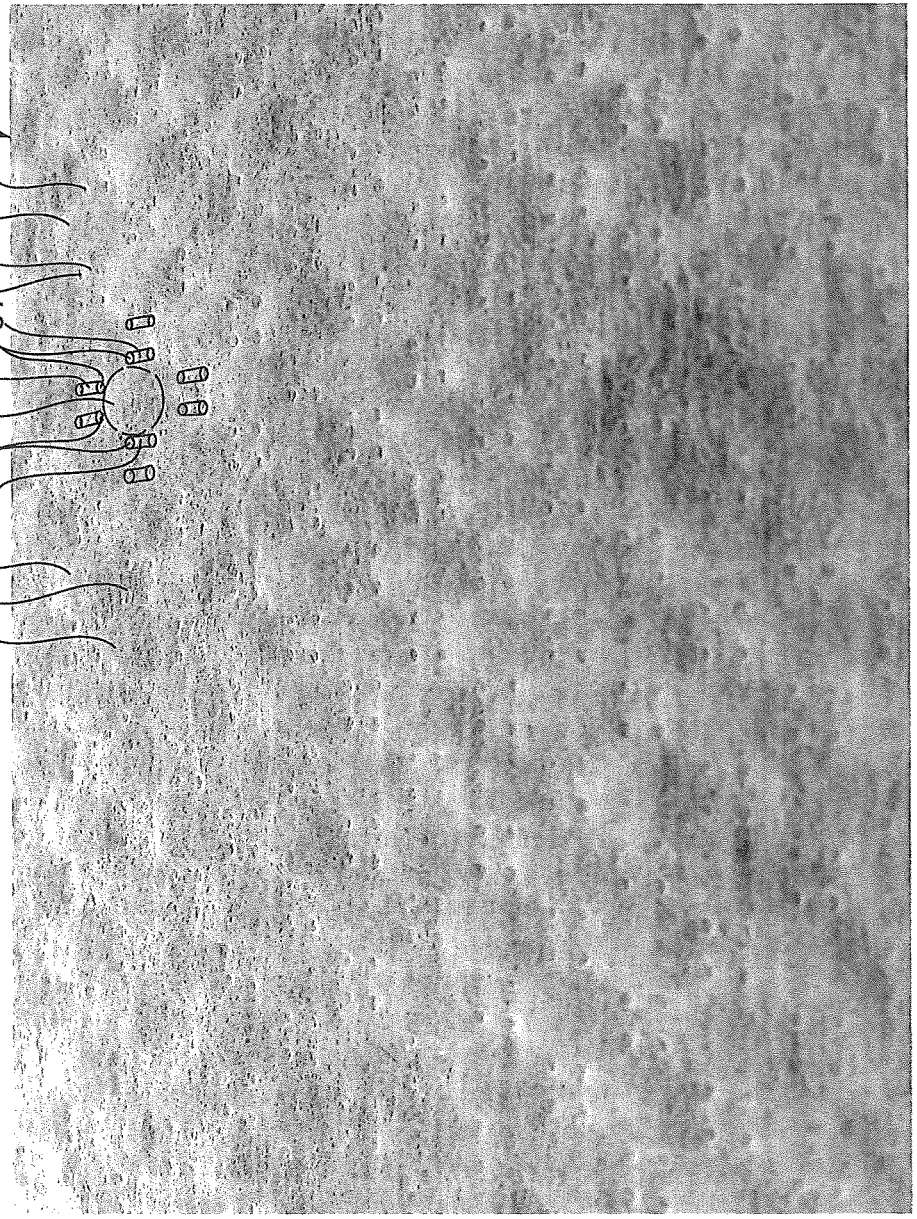
FIG. 15 is a picture taken from substantially top of an assembled body of the topsheet and the intermediate sheet.
Figure 16:
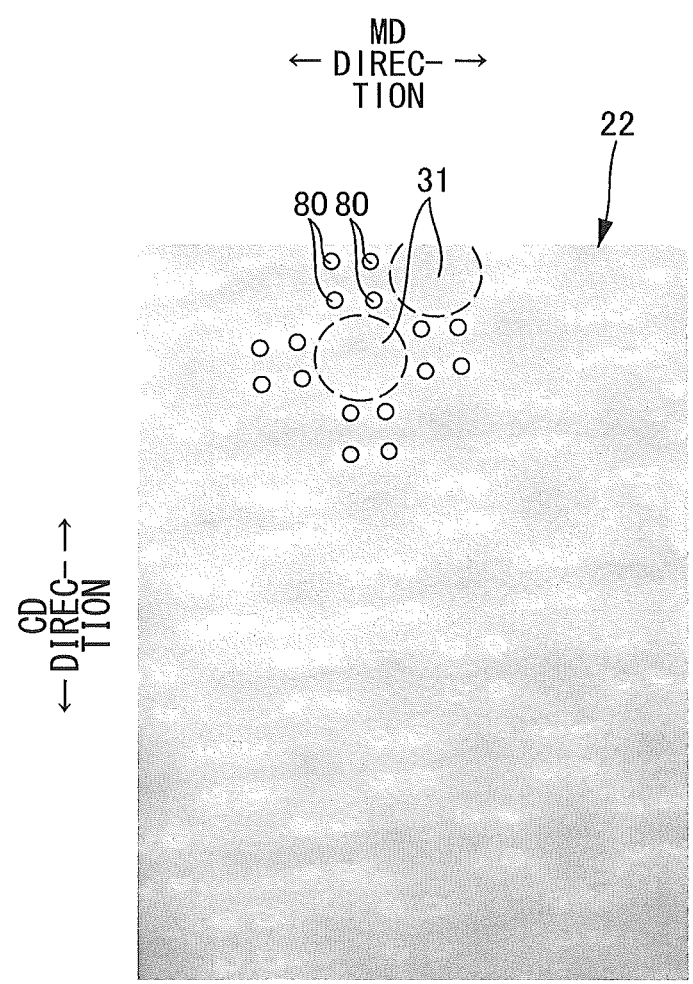
FIG. 16 is a picture of a surface of a topsheet of a comparative sample.

FIG. 15 illustrates a sample picture of an assembled body of the topsheet 22 and the intermediate sheet 25 in which the pattern illustrated in FIG. 10 and FIG. 12-(b) is adopted. FIG. 16 is a picture obtained by photographing a surface of a topsheet of a comparative sample.

As such, by adopting a characteristic bonding pattern at the space between the convex portions 31 that are adjacent in the MD direction, as is clear from the sample illustrated in FIG. 15 and the sample illustrated in FIG. 16, even when a vertical line (wrinkle) is formed when forming the convex portions 31, when bonding with the intermediate sheet 25, the topsheet bonding portions 80 by pressing and welding and the pressed portions 81 by pressing without welding are continuously alternately formed in the CD direction such that to across the vertical line. Thus, the topsheet bonding portions 80 can be formed to largely extend the vertical line, and such a state or a nearly state can be retained even after the product is manufactured. Further, as the finally bonded portions are intermittently provided in the CD direction, lowering of flexibility and worsening of an appearance can be prevented. On the other hand, in the comparative sample provided with the topsheet bonding portions 80 which do not satisfy the above described condition, a number of wrinkles each extending along the MD direction are formed with spaces in the CD direction, and an appearance is worsened.

The bonding pattern is not particularly limited as long as the plurality of topsheet bonding portions 80 are aligned in the CD direction with spaces their between at the region between the convex portions 31 that are adjacent in the MD direction, and the space between the topsheet bonding portions 80 in the CD direction is connected by the pressed portion 81. For example, as illustrated in FIG. 11-(*b*) FIG. 12-(*a*), it is preferable that the topsheet bonding portion 80 is also formed at a center position in the CD direction corresponding to a center portion in the CD direction between the convex portions 31 that are adjacent in the MD direction in order to prevent formation of wrinkles. In such a case, it is preferable to make an area of the topsheet bonding portion 80 at the center position in the CD direction to be smaller than those of other topsheet bonding portions 80 in a viewpoint of flexibility. Meanwhile, for example, as illustrated in FIG. 11-(*a*) and FIG. 12-(*b*), it is preferable to make a pattern in which the topsheet bonding portion 80 is not formed at the center position in the CD direction for improving flexibility.

Further, in addition to a case in which a single line of a plurality of the topsheet bonding portions 80 that are aligned with spaces in the CD direction is provided at the region between the convex portions 31 that are adjacent in the MD direction as illustrated in FIG. 11-(*a*) and FIG. 11-(*b*), a plurality of such lines may be provided with a space in the MD direction as illustrated in FIG. 10, FIG. 12-(*a*) and FIG. 12-(*b*). The former case is appropriate for the pattern in which the space between the convex portions 31 in the MD direction is narrow such as the embodiment where the convex portions 31 are aligned in a matrix form as illustrated in FIG. 11-(*a*) and FIG. 11-(*b*), and the latter case is appropriate for the pattern in which the space between the convex portions 31 in the MD direction is wide such as the embodiment where the convex portions 31 are aligned in a staggered form as illustrated in FIG. 10, FIG. 12-(*a*) and FIG. 12-(*b*). Here, for the latter embodiment, although the topsheet 22 and the intermediate sheet 25 may not be welded and pressed at the space portion of the topsheet bonding portions 80 in the MD direction similarly as the space portion in the CD direction, if the topsheet 22 and the intermediate sheet 25 are not welded and also the topsheet 22 is pressed less than the space portion in the CD direction (including a non-pressed state, where not pressed at all), better flexibility and appearance can be obtained.

The shape of each of the topsheet bonding portions is not specifically limited, and any shapes may be used such as an elliptical shape, a polygonal shape, a star shape, a cloud shape in addition to the circular shape as the illustrated example.

Although the size of the topsheet bonding portion 80 may be properly determined, it is preferable that each of the topsheet bonding portions 80 between the convex portions 31 that are adjacent in the MD direction is a point-like bonding portion whose length 80*m* in the MD direction is approximately 0.1 to 0.4 times (normally, 0.5 to 3 mm, for example) of a distance 31*y* in the MD direction between centers of the convex portions 31 of the CD direction lines that are adjacent in the MD direction, and whose length 80*c* in the CD direction is approximately 0.1 to 0.4 times (normally, 0.5 to 3 mm, for example) of a distance 31*x* in the CD direction between centers of the convex portions 31 of the MD direction lines that are adjacent in the CD direction. Further, it is preferable that a distance 80*d* in the CD direction between the topsheet bonding portions 80 that are adjacent in the CD direction is approximately 1 to 5 times (normally, 0.5 to 15 mm, for example) of the distance 80*c* in the CD direction of the topsheet bonding portion 80. It is preferable that the number of the topsheet bonding portions 80 in each of the CD direction lines is approximately 2 to 4.

Further, as illustrated in FIG. 12-(*a*) and FIG. 12-(*b*), when the convex portions 31 are formed in a staggered form, as the region between the convex portions 31 that are adjacent in the CD direction is also a region between the convex portions 31 that are adjacent in the MD direction, the topsheet bonding portions 80 similar to those provided between the convex portions 31 that are adjacent in the MD direction are provided. On the other hand, as illustrated in FIG. 11-(*a*) and FIG. 11-(*b*), when the convex portions 31 are formed in a matrix form, separately from the topsheet bonding portions 80 formed between the convex portions 31 that are adjacent in the MD direction, the topsheet bonding portions 80 are intermittently provided in the MD direction between the convex portions 31 that are adjacent in the CD direction. Although a pattern of the topsheet bonding portions 80 between the convex portions 31 that are adjacent in the CD direction is not specifically limited, it is preferable that the point-like topsheet bonding portions 80 are aligned with a space therebetween in the MD direction. As illustrated in FIG. 11-(*b*), similar to the space portion in the CD direction, the pressed portion 81 may be provided at a space portion in the MD direction. This MD direction line of the topsheet bonding portions 80 may be singularly provided at an intermediate position of the convex portions 31 that are adjacent in the CD direction as the illustrated example, and alternatively, a plurality of the MD direction lines of the topsheet bonding portions 80 may be provided with a space in the CD direction. Further, although the size of the point-like topsheet bonding portion 80 is not specifically limited, it is preferable that the length 80*m* in the MD direction is approximately 0.1 to 0.4 times (normally, 0.5 to 3 mm, for example) of the distance 31*y* between centers of the convex portions 31 of the CD direction lines that are adjacent in the MD direction, and the length 80*c* in the CD direction is approximately 0.1 to 0.4 times (normally, 0.5 to 3 mm, for example) of the distance 31*x* in the CD direction between centers of the convex portions 31 of the MD direction lines that are adjacent in the CD direction.

The topsheet bonding portions 80 are formed by intermittent bonding patterns in the width direction and in the front and rear direction, and a space in each of the directions may be properly determined. For example, it is preferable that a bonding range A3 in the CD direction by the topsheet bonding portions 80 between the convex portions 31 that are adjacent in the MD direction is approximately 0.3 to 1 times (normally, 1 to 10 mm, for example) of the distance 31*x* in the CD direction between centers of the convex portions 31 of the MD direction lines that are adjacent in the CD direction. Further, a bonding range A4 in the MD direction by the topsheet bonding portions 80 between the convex portions 31 that are adjacent in the CD direction is approximately 0.3 to 1 times (normally, 1 to 10 mm, for example) of the distance 31*y* in the MD direction between centers of the convex portions 31 of the CD direction lines that are adjacent in the MD direction. If these bonding range A3 in the CD direction and the bonding range A4 in the MD direction are too wide, such a structure is the same as a structure in which the topsheet bonding portions 80 are continuously formed in the CD direction and in the MD direction, respectively, and permeability and flexibility of the topsheet 22 may be lowered.

Figure 14:
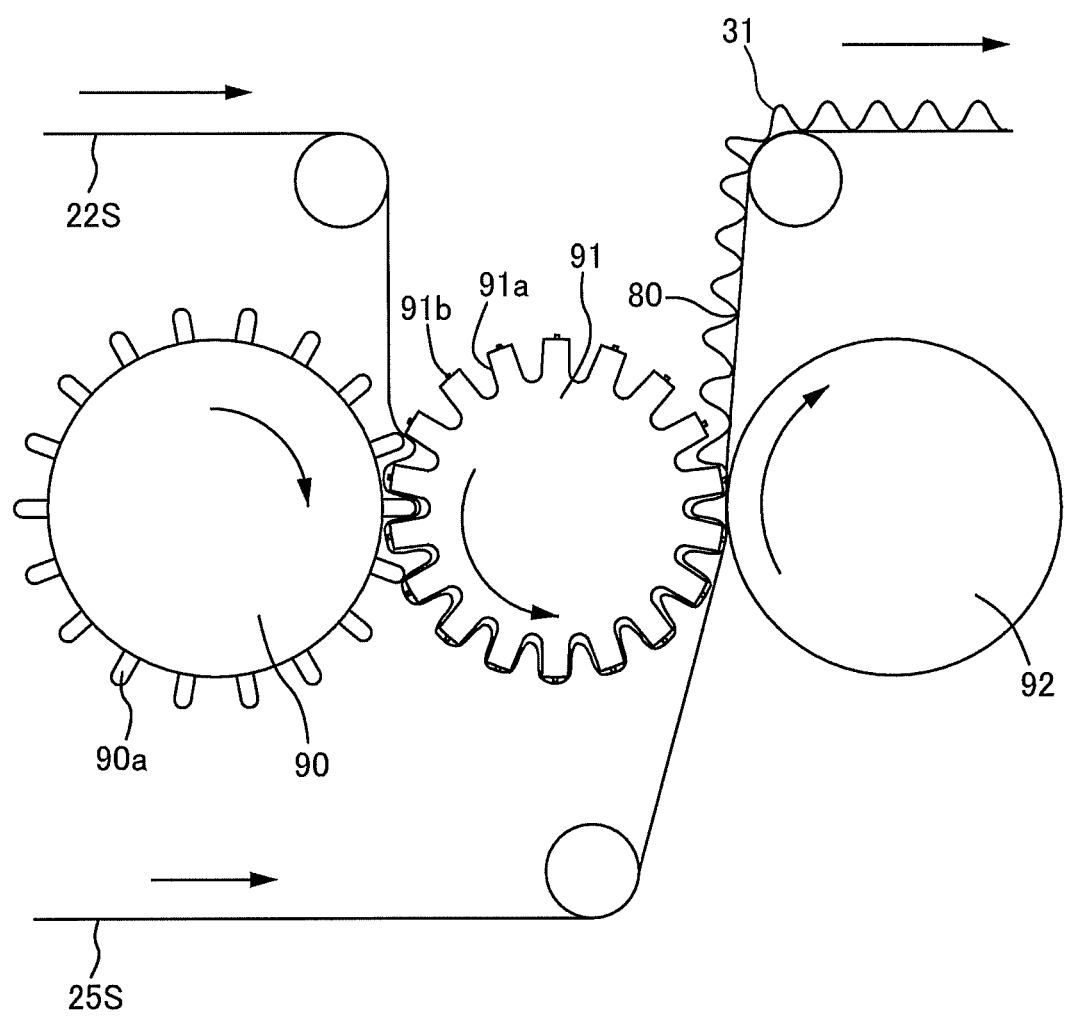
FIG. 14 is a view for describing an example of a processing plant of the topsheet and an intermediate sheet.

FIG. 14 illustrates a processing plant for forming the above described convex portions. The plant includes a pushing roller 90, a concave roller 91 facing the pushing roller 90, and a bonding roller 92 facing the concave roller 91. FIG. 17-(*a*) and FIG. 17-(*b*) are views illustrating the pushing roller 90. FIG. 18-(a) and FIG. 18-(b) are views illustrating the concave roller 91.

As illustrated in FIG. 17-(a) and FIG. 17-(b), a number of pushing convex portions 90a are formed at a peripheral surface of the pushing roller 90 in the above described alignment pattern of the convex portions 31. Although the shape of the convex portion of the pushing roller 90 may be properly determined, it is preferable that the shape is a frustum (circular truncated cone) having a cross-section (circular shape, elliptical shape, regular polygonal shape or the like, for example) corresponding to the shape of the convex portion 31 to be formed.

As illustrated in FIG. 18-(a) and FIG. 18-(b), pushdown concave portions 91a respectively corresponding to the pushing convex portions 90a of the pushing roller 90 are formed at a peripheral surface of the concave roller 91, and bonding convex portions 91b and a compressing convex portion 91e are formed between each adjacent pushdown concave portions 91a. The bonding convex portion 91b is a portion for forming the topsheet bonding portion 80 in the above described bonding pattern, and the compressing convex portion 91e is a portion for compressing a non-woven-fabric 22S which becomes the topsheet 22 in a thickness direction at a portion between the topsheet bonding portions 80 in the CD direction without welding the topsheet 22 and a material 25S of the intermediate sheet. When the material 25S of the intermediate sheet is one that is compressed in the thickness direction such as a non-woven-fabric, the intermediate sheet 25 is also compressed by the compressing convex portion 91e. More in detail, in this concave roller 91, at a region between the pushdown concave portions 91a that are adjacent in the circumferential direction of the roller, a line in which a plurality of the bonding convex portions 91b are aligned with a space in the axis direction of the roller is formed such that across a center position of the region in the axis direction of the roller, and a space portion between the bonding convex portions 91b in the axis direction of the roller is formed as the compressing convex portion 91e. Although the material is not compressed at portions other than the bonding convex portions 91b, the compressing convex portions 91e and the pushdown concave portions 91a, the portions may be compressed similarly as the compressing convex portions 91e or less than the compressing convex portions 91e. As long as the convex portion is formed, the pushdown concave portion 91a of the concave roller 91 may be an "open hole (aperture)" without a bottom surface having a size that the pushing convex portion can enter, and the "pushdown concave portion 91a" includes such an "open hole (aperture)".

The size, the shape and the arrangement of the pushing convex portion 90a of the pushing roller 90 correspond to the size, the shape and the arrangement of an inner space of the convex portion 31 to be formed, and the size, the shape and the arrangement of the pushdown concave portion 91a of the concave roller 91 correspond to the size, the shape and the arrangement of an outer shape of the convex portion 31 to be formed. Further, the size, the shape and the arrangement of the bonding convex portion 91b of the concave roller 91 correspond to the size, the shape and the arrangement of the topsheet bonding portion 80 to be formed, and the size, the shape and the arrangement of the compressing convex portion 91e of the concave roller 91 correspond to the size, the shape and the arrangement of the pressed portion 81 when the pressed portion 81 is formed. Thus, these size, shape and arrangement may be similarly changed to the size, the shape and the arrangement of the above described convex portion 31, the topsheet bonding portion and the pressed portion. For example, the length 91m in the MD direction, the length 91c in the CD direction and the distance 91d in the CD direction of the compressing convex portion 91c in the embodiment illustrated in FIG. 18-(b) may be within the ranges similar to the length 80m in the MD direction, the length 80c in the CD direction and the distance 80d in the CD direction of the topsheet bonding portion 80 illustrated in FIG. 12-(b).

Figure 19:
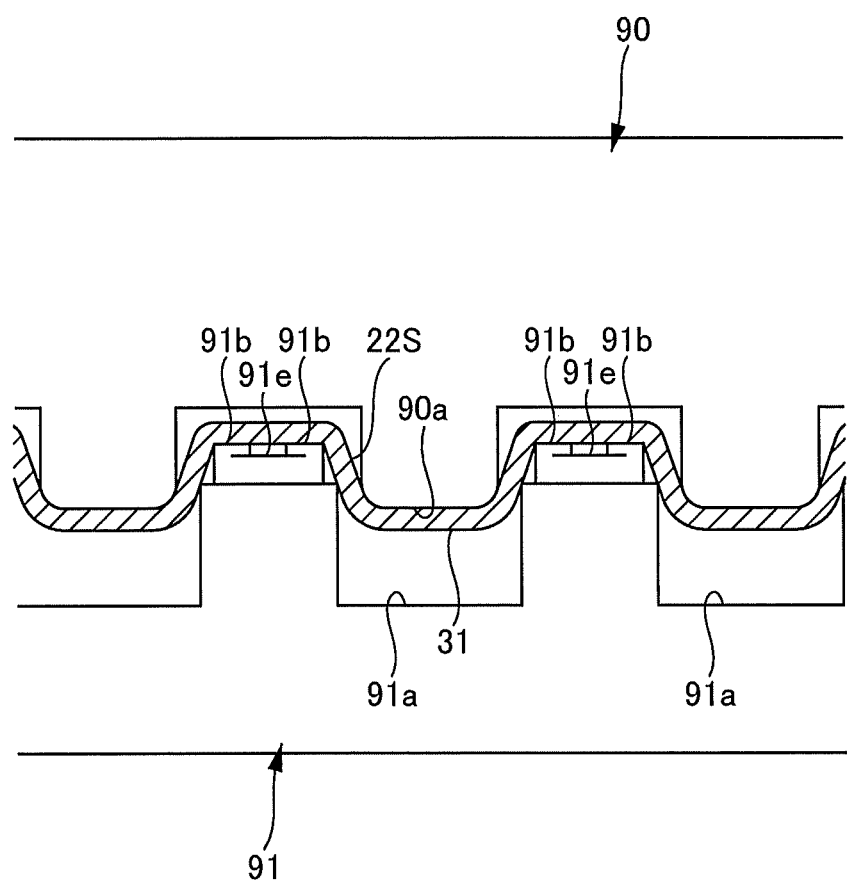
FIG. 19 is an enlarged cross-sectional view illustrating a main part of a forming step of a convex portion by the pushing roller and the concave roller.

FIG. 19 is an enlarged cross-sectional view illustrating a main part of a forming step of the convex portion by the pushing roller 90 and the concave roller 91. When processing, as illustrated in FIG. 19, the non-woven-fabric 22S which becomes the topsheet 22 is sandwiched between the pushing roller 90 and the concave roller 91 while transferring it by drawing from downstream of a manufacturing line, and the convex portions 31 are formed by embossing by which the convex portions of the pushing roller 90 are pushed into the pushdown concave portions 91a of the concave roller 91, respectively.

Thereafter, while guiding the non-woven-fabric 22S in which the convex portions 31 are formed by being wound around the concave roller 91, the material 25S of the intermediate sheet is transferred to outside of the non-woven-fabric which becomes the topsheet 22 by drawing from downstream of the manufacturing line. Then, as illustrated in FIG. 20-(a) and FIG. 20-(b), the non-woven-fabric 22S which becomes the topsheet 22 and the material 25S of the intermediate sheet are sandwiched between the concave roller 91 and the bonding roller 92, compressed between the compressing convex portions 91e of the concave roller 91 and the peripheral surface of the bonding roller 92, and heated to be welded between the bonding convex portions 91b of the concave roller 91 and the peripheral surface of the bonding roller 92. With this, the topsheet bonding portions 80 are formed, and an assembled body of the topsheet 22 and the intermediate sheet 25 is manufactured. With this, even when a vertical line (wrinkle) is formed in the non-woven-fabric 22S which becomes the topsheet 22 between the convex portions 31 that are adjacent in the MD direction when forming the convex portions 31, pressed and welded portions 80 and pressed portions 81 that are pressed but not welded are continuously alternately provided in the CD direction such that to across the vertical line, when bonding with the material 25S of the intermediate sheet. Thus, the topsheet bonding portions 80 can be formed to largely extend the vertical line, and such a state or a nearly state can be retained even after the product is manufactured. Further, as the finally bonded portions are intermittently provided in the CD direction, lowering of flexibility and worsening of an appearance can be prevented. Here, as can be understood from this principle, even when a trace compressed by the compressing convex portion 91e does not remain almost at all or does not remain at all, in addition to a case that the trace remains as the pressed portion 81, an effect of preventing the vertical line can be obtained.

Any pressing and welding means capable of pressing a material in its thickness direction and welding it may be adopted such as ultrasonic sealing in addition to heat seal by which a roller is heated to weld the material. A disposal diaper may be manufactured by imposing the processed assembled body of the topsheet 22 and the intermediate sheet 25 to an absorbent body and the like by a known method.

As described in the above embodiments, according to a processing method in which the topsheet is bonded with a material of the intermediate sheet 25 right after forming the convex portions 31 without having a period for absorbing a wrinkle, the wrinkle tends to remain more. Thus, it is preferable to adopt the above described bonding pattern. Of course, if the topsheet bonding portions 80 are formed after forming the convex portions 31 by embossing, another plant other than the above described processing plant including the three rollers. Further, although the non-woven-fabric that becomes the topsheet 22 is directly sent to a site where the pushing roller 90 and the concave roller 91 engage with each other in the illustrated example, the non-woven-fabric that becomes the topsheet 22 may be sent from a tangent line direction of the peripheral surface of the pushing roller 90 to be only wound around the pushing roller 90, and may be guided to transfer to the peripheral surface of the concave roller 91 while being sandwiched between the concave roller 91.

Further, instead of the slit 40 that penetrates the absorbent body 23 in its thickness direction as described in the embodiment, the same merits can be obtained in an embodiment in which a concave portion that is concaved from a top side to a back side is provided. Such a concave portion may be formed by partially compressing the absorbent body such as by embossing, and alternatively, may be formed by partially making mass per unit area of a material low. However, as the slit 40 is more easily collapsed in the width direction, it is appropriate to adapt the present invention to the slit 40.

(Description Regarding Terms in Specification)

When following terms are used in the specification, unless otherwise described in the specification, the terms have following meanings, respectively.

The "front and rear (longitudinal) direction" means a direction connecting a ventral side (front side) and a dorsal side (rear side), and the "width direction" means a direction (lateral direction) that is perpendicular to the front and rear direction.

The "spread state" means a state evenly spread without contraction and looseness.

The "extension percentage" means a value assuming that its natural length is 100%.

The "weight per unit area" is measured as follows. After a sample or a test piece is preliminary dried, the sample or the like is left in a laboratory or an apparatus of a standard condition (temperature 20±5° C. and relative humidity less than or equal to 65% at the test place) to be constant mass. The preliminary drying means to make the sample or the test piece to be constant mass under environment in which the relative humidity is 10 to 25% and the temperature does not exceed 50° C. Here, for the fiber whose official moisture regain is 0.0%, it is unnecessary to perform the preliminary drying. A sample whose size is 200 mm×250 mm (±2 mm) is cut from the test piece at the constant mass using a paper density plate (200 mm×250 mm, ±2 mm). The gravity of the sample is measured, and weight per unit area is obtained by multiplying the measured value by 20 times and calculating the weight per square meter.

The "thickness" of each of the topsheet 22 and the intermediate sheet 25 illustrated in FIG. 10 to FIG. 20-(b) means an apparent thickness, and is measured by a method described at paragraph 0017 of Japanese Patent No. 3611838. Specifically, when measuring, a measurement piece of length 30 mm×width 30 mm is cut under a state that the topsheet 22 and the intermediate sheet 25 are bonded. Then, a cut surface is formed by a line that is substantially in parallel to a vertical line (a fiber orientation direction (a flowing direction in manufacturing the non-woven-fabric) of a non-woven-fabric (fiber aggregation) that constitutes the topsheet 22) and also passes on the topsheet bonding portion 80. An enlarged picture of this cut surface is obtained by a digital microscope VHX-1000 manufactured by KEYENCE CORPORATION or the like, an apparent maximum thickness of the topsheet 22 is obtained based on this enlarged picture as the thickness of the topsheet 22, and an apparent thickness of the intermediate sheet 25 is measured at a measurement site of the maximum thickness of the topsheet 22 as the thickness of the intermediate sheet 25. Further, the size in the cross-sectional direction such as the thickness of other sites (the thickness of the topsheet bonding portion 80, the thickness of the pressed portion 81 and the like) or the height 31z of the convex portion 31 is measured similarly as the measurement of the "thickness" of the topsheet and the intermediate sheet and the protrusion height of the convex portion from a bottom portion to a top portion (an apex) is measured.

The "thickness" of the absorbent body is measured using a thickness gauge (PEACOCK, Large type Dial Thickness Gauge, J-B (measurement range 0 to 35 mm) or K-4 (measurement range 0 to 50 mm)) manufactured by OZAKI MFG. CO., LTD. while horizontally maintaining the sample and the thickness gauge.

The "thickness" other than above is automatically measured using an automatic thickness gauge (KES-G5 handy compression measurement program) under a condition of load: 10 gf/cm$^2$, and pressed area: 2 cm$^2$.

When an environmental condition of a test or a measurement is not described, it is assumed that the test or the measurement is conducted in a laboratory or an apparatus under a standard condition (temperature 20±5° C. and relative humidity less than or equal to 65% at the test place).

The size of each part means the size at the spread state, not a natural length, unless otherwise described.

Hereinafter, preferable embodiments of the invention are described.

(Clause 1)

An absorbent article including:

a crotch portion;

a front side portion and a rear side portion that are extended toward a front side and a rear side of the crotch portion, respectively;

an absorbent body provided at a front and rear direction range including the crotch portion; and a topsheet that covers a top side of the absorbent body, wherein a concave groove with a predetermined width that is concaved from a top surface to a back side or a slit with a predetermined width is formed in the absorbent body at least at the crotch portion to extend in a front and rear direction, and wherein the topsheet includes a fall-in portion that is fallen in the concave groove or the slit of the absorbent body, and convex portions are provided at least at a part of the fall-in portion.

(Effects)

According to the absorbent article of the invention, even when the space in the concave groove or the slit becomes narrow, as the convex portion that is positioned at a bottom portion of the fall-in portion is sandwiched by facing side surfaces, a space can be retained between the facing side surfaces above the convex portion, or as the convex portion that is positioned at one of the facing side surfaces contact the other of the facing side surfaces, a space can be retained between the periphery of the convex portion and the facing side surface. Thus, collapse of the concave groove or the slit can be suppressed, and an effect of improving diffusibility by the slit or the concave groove can be retained.

Here, the term "slit" means a portion that penetrates a top surface to a back surface of the absorbent body. Further, "with a predetermined width" regarding the slit just means that a concave groove or a slit that does not have a width (a case when the facing side walls contact) is not included, and does not mean that the width is constant. Thus, as long as the concave groove or the slit includes a width, the concave groove or the slit whose width varies is also included.
(Clause 2)

The absorbent article according to clause 1,
wherein a number of the convex portions are aligned with a space therebetween in a width direction and in the front and rear direction at a range that includes the fall-in portion and that is larger than the fall-in portion at the topsheet,
wherein a plurality of lines, in each of which the convex portions are aligned in the front and rear direction, is formed in the fall-in portion,
wherein the size of the convex portion in the front and rear direction is larger than a space between the convex portions that are adjacent in the front and rear direction, and
wherein the size of the convex portion in the width direction is larger than a space between the convex portions that are adjacent in the width direction.
(Effects)

The convex portions of the topsheet may be only provided in the fall-in portion, in other words, only provided in the slit or in the concave groove. However, it is difficult to manufacture such that the position of the convex portion matches the position of the slit or the concave groove of the absorbent body. On the other hand, if the number of convex portions are aligned at a broader range that includes the fall-in portion and also a plurality of lines in each of which the convex portions are aligned in the front and rear direction are formed, as defined in this clause, even when the position of the topsheet in the width direction is slightly shifted with respect to the absorbent body when being manufactured or when being used, either of the lines of the convex portions that exists in the concave groove or the slit can retain the space of the concave groove or the slit. Further, if the size of the convex portion is small and the distance between the convex portions is too large, or the convex portion can fit the space between the adjacent convex portions, the above described function of retaining the space may not be obtained. On the other hand, if the size of the convex portion is larger than the space between the convex portions, area occupied by the convex portions becomes relatively larger than that by the space between the convex portions. Thus, in any arrangements, and also even if the fall-in portion is deformed in any shapes, the convex portion of one of the facing side surfaces does not enter the space between the convex portions of the other of the facing side surfaces, and the facing convex portions contact with each other to ensure preferable spaces.
(Clause 3)

The absorbent article according to clause 2, wherein the convex portions are aligned in a matrix form, and a space between the convex portions that are adjacent in the width direction is 0.1 to 0.5 times of the size of the convex portion in the width direction.
(Effects)

When the convex portions are aligned in a matrix form, a portion between the convex portions (a portion with low rigidity) linearly continuously extend longest in the front and rear direction at the space between the convex portions that are adjacent in the width direction. Thus, when the width of the slit or the concave portion is narrowed, the topsheet is bent at this position. Thus, it is preferable that the convex portions are aligned at the size and the space of this clause, because the convex portion of one of the facing side surfaces does not enter the space between the convex portions of the other of the facing side surfaces so easily, and the facing convex portions contact with each other.
(Clause 4)

The absorbent article according to clause 2, wherein the convex portions are aligned in a staggered form, and a space between the convex portions that are adjacent in the width direction is 0.5 to 0.9 times of the size of the convex portion in the width direction.
(Effects)

When the convex portions are aligned in a staggered form, a portion between the convex portions (a portion with low rigidity) linearly continuously extend longest in the front and rear direction at a center in the width direction of the convex portions that are aligned in a zig-zag manner in the front and rear direction. Thus, when the width of the slit or the concave portion is narrowed, the topsheet is bent at this position. Thus, it is preferable that the convex portions are aligned at the size and the space of this clause, because the convex portion of one of the facing side surfaces does not enter the space between the convex portions of the other of the facing side surfaces so easily, and the facing convex portions contact with each other.

INDUSTRIAL APPLICABILITY

The present invention can be used for a general absorbent article such as a sanitary napkin in addition to a disposal diaper such as a pad type disposal diaper, a pull-up type or a tape type disposal diaper.

The present application is based on and claims the benefit of priority of Japanese Priority Application No. 2015-188221 filed on Sep. 25, 2015, the entire contents of which are hereby incorporated by reference.

NUMERALS

B2 . . . rear side portion, C2 . . . crotch portion, F2 . . . front side portion, 11 . . . convex portion arrangement region, 21 . . . liquid impermeable sheet, 22 . . . topsheet, 23 . . . absorbent body, 24 . . . standing gather, 24s . . . gather sheet, 25 . . . intermediate sheet, 26 . . . packaging sheet, 27 . . . exterior sheet, 30 . . . fall-in portion, 31 . . . convex portion, 40 . . . slit, 41 . . . another slit, 200 . . . pad type disposal diaper.

What is claimed is:

1. An absorbent article comprising:
   a crotch portion;
   a front side portion and a rear side portion that are extended toward a front side and a rear side of the crotch portion, respectively;
   an absorbent body provided at a front and rear direction range including the crotch portion, and
   a topsheet that covers a top side of the absorbent body,
   wherein a concave groove with a predetermined width that is concaved from a top surface to a back side or a slit with a predetermined width is formed in the absorbent body at least at the crotch portion to extend in a front and rear direction, said concave groove or the slit being configured to completely penetrate the absorbent body in a thickness direction thereof,
   wherein the topsheet includes a fall-in portion that is fallen in the concave groove or the slit of the absorbent body, and convex portions are provided at least at a part of the fall-in portion only on a surface that is adapted to directly contact a user of the absorbent article when the user wears the absorbent article, and wherein the convex portions have heights of 0.8 to 2.0 mm.

2. The absorbent article according to claim 1, wherein a number of the convex portions are aligned with a space therebetween in a width direction and in the front and rear direction at a range that includes the fall-in portion and that is larger than the fall-in portion at the topsheet, wherein a plurality of lines, in each of which the convex portions are aligned in the front and rear direction, is formed in the fall-in portion, wherein the size of the convex portion in the front and rear direction is larger than a space between the convex portions that are adjacent in the front and rear direction, and wherein the size of the convex portion in the width direction is larger than a space between the convex portions that are adjacent in the width direction.

3. The absorbent article according to claim 2, wherein the convex portions are aligned in a matrix form, and a space between the convex portions that are adjacent in the width direction is 0.1 to 0.5 times of the size of the convex portion in the width direction.

4. The absorbent article according to claim 2, wherein the convex portions are aligned in a staggered form, and a space between the convex portions that are adjacent in the width direction is 0.5 to 0.9 times of the size of the convex portion in the width direction.

5. The absorbent article according to claim 1, wherein the convex portions are provided only within the fall-in portion of the top sheet.

* * * * *